US012723231B2

(12) United States Patent
Mireles et al.

(10) Patent No.: US 12,723,231 B2
(45) Date of Patent: Sep. 1, 2026

(54) PHAGE-RESISTANT MICROORGANISMS

(71) Applicant: INNOVACION Y DESARROLLO DE ENERGIA ALFA SUSTENTABLE S.A. DE C.V., Nuevo Leon (MX)

(72) Inventors: Ivan Alejandro de la Pena Mireles, Monterrey (MX); Claudio Garibay Orijel, Metepec (MX); Liliana Dondiego Rodriguez, Toluca (MX); Javier Acedo Zuniga, Mexico City (MX)

(73) Assignee: INNOVACION Y DESARROLLO DE ENERGIA ALFA SUSTENTABLE S.A. DE C.V., Nuevo Leon (MX)

(*) Notice: Subject to any disclaimer, the term of this patent is extended or adjusted under 35 U.S.C. 154(b) by 439 days.

(21) Appl. No.: 17/777,878

(22) PCT Filed: Nov. 27, 2019

(86) PCT No.: PCT/IB2019/001262

§ 371 (c)(1),
(2) Date: May 18, 2022

(87) PCT Pub. No.: WO2021/105733

PCT Pub. Date: Jun. 3, 2021

(65) Prior Publication Data

US 2022/0411746 A1 Dec. 29, 2022

(51) Int. Cl.

| | |
|---|---|
| ***C12N 1/20*** | (2026.01) |
| ***C12N 1/205*** | (2026.01) |
| ***C12N 15/70*** | (2006.01) |
| ***C12Q 1/10*** | (2006.01) |
| *C12R 1/19* | (2006.01) |

(52) U.S. Cl.

CPC ............. *C12N 1/205* (2021.05); *C12N 15/70* (2013.01); *C12Q 1/10* (2013.01); *C12N 2800/101* (2013.01); *C12R 2001/19* (2021.05)

(58) Field of Classification Search

CPC .. C12N 1/205; C12N 15/70; C12N 2800/101; C12N 1/20; C12Q 1/10; C12Q 1/04; C12R 2001/19; C07K 14/245

See application file for complete search history.

(56) References Cited

U.S. PATENT DOCUMENTS

2007/0065913 A1 3/2007 Chen et al.

FOREIGN PATENT DOCUMENTS

| | | | | |
|---|---|---|---|---|
| CN | 103013871 A | 4/2013 | | |
| CN | 109762770 A | 5/2019 | | |
| CN | 110396533 A | 11/2019 | | |
| CN | 117187126 A | 12/2023 | | |
| JP | S61132179 A | 6/1986 | | |
| JP | H01080280 A | 3/1998 | | |
| WO | WO-2011125015 A2 * | 10/2011 | ............. | A61K 47/42 |
| WO | WO-2012090022 A1 * | 7/2012 | ............... | C12N 1/20 |

OTHER PUBLICATIONS

Chatterjee S, Rothenberg E. Interaction of bacteriophage I with its *E. coli* receptor, LamB. Viruses. Nov. 15, 2012;4(11):3162-78. doi: 10.3390/v4113162. PMID: 23202520; PMCID: PMC3509688. (Year: 2012).*

Guentzel MN. *Escherichia*, Klebsiella, Enterobacter, Serratia, Citrobacter, and Proteus. In: Baron S, editor. Medical Microbiology. 4th edition. Galveston (TX): University of Texas Medical Branch at Galveston; 1996. Chapter 26. Available from: https://www.ncbi.nlm.nih.gov/books/NBK8035/ (Year: 1996).*

Fischer CR, Yoichi M, Unno H, Tanji Y. The coexistence of *Escherichia coli* serotype O157:H7 and its specific bacteriophage in continuous culture. FEMS Microbiol Lett. Dec. 15, 2004;241(2):171-7. doi: 10.1016/j.femsle.2004.10.017. PMID: 15598529. (Year: 2004).*

Harcombe WR, Bull JJ. Impact of phages on two-species bacterial communities. Appl Environ Microbiol. Sep. 2005;71(9):5254-9. doi: 10.1128/AEM.71.9.5254-5259.2005. PMID: 16151111; PMCID: PMC1214695. (Year: 2005).*

Kudva IT, Jelacic S, Tarr PI, Youderian P, Hovde CJ. Biocontrol of *Escherichia coli* 0157 with O157-specific bacteriophages. Appl Environ Microbiol. Sep. 1999;65(9):3767-73. doi: 10.1128/AEM.65.9.3767-3773.1999. PMID: 10473373; PMCID: PMC99698. (Year: 1999).*

Li P, Lin H, Mi Z, Xing S, Tong Y, Wang J. Screening of Polyvalent Phage-Resistant *Escherichia coli* Strains Based on Phage Receptor Analysis. Front Microbiol. Apr. 18, 2019;10:850. doi: 10.3389/fmicb.2019.00850. PMID: 31105661; PMCID: PMC6499177. (Year: 2019).*

Mizuno K, et al. Adjacent-possible ecological niche: growth of Lactobacillus species co-cultured with *Escherichia coli* in a synthetic minimal medium. Sci Rep. Oct. 16, 2017;7(1):12880. doi: 10.1038/s41598-017-12894-3. PMID: 29038545; PMCID: PMC564 (Year: 2017).*

Mizoguchi K, Morita M, Fischer CR, Yoichi M, Tanji Y, Unno H. Coevolution of bacteriophage PP01 and *Escherichia coli* O157:H7 in continuous culture. Appl Environ Microbiol. Jan. 2003;69(1):170-6. doi: 10.1128/AEM.69.1.170-176.2003. PMID: 12513992; PMCID: PMC152390. (Year: 2003).*

Montso PK, Mlambo V, Ateba CN. Characterization of Lytic Bacteriophages Infecting Multidrug-Resistant Shiga Toxigenic Atypical *Escherichia coli* O177 Strains Isolated From Cattle Feces. Front Public Health. Nov. 26, 2019;7:355. doi: 10.3389/fpubh.2019.00355. PMID: 32039126; PMCID: PMC6988782. (Year: 2019).*

Tanji Y, Shimada T, Yoichi M, Miyanaga K, Hori K, Unno H. Toward rational control of *Escherichia coli* O157:H7 by a phage cocktail . Appl Microbiol Biotechnol. Apr. 2004;64(2):270-4. doi: 10.1007/s00253-003-1438-9. Epub Sep. 12, 2003. PMID: 13680205. (Year: 2004).*

(Continued)

*Primary Examiner* — Sharmila G Landau
*Assistant Examiner* — Natalie Iannuzo
(74) *Attorney, Agent, or Firm* — TUCKER ELLIS LLP; J. Derek Mason

(57) ABSTRACT

Genetically modified microorganisms which are resistant to infection by bacteriophages and that retain their kinetic parameters and methods of making the same.

5 Claims, 14 Drawing Sheets

Specification includes a Sequence Listing.

(56) References Cited

OTHER PUBLICATIONS

Hancock RE, Reeves P. Bacteriophage resistance in *Escherichia coli* K-12: general pattern of resistance. J Bacteriol. Mar. 1975;121 (3):983-93. doi: 10.1128/jb.121.3.983-993.1975. PMID: 1090611; PMCID: PMC246027. (Year: 1975).*

Rotman E, Kouzminova E, Plunkett G 3rd, Kuzminov A. Genome of Enterobacteriophage Lula/phi80 and insights into its ability to spread in the laboratory environment. J Bacteriol. Dec. 2012;194(24):6802-17. doi: 10.1128/JB.01353-12. Epub Oct. 5, 2012. PMID: 23042999; PMCID: PMC3510586. (Year: 2012).*

Peng, Q., Yuan, Y. Characterization of a newly isolated phage infecting pathogenic *Escherichia coli* and analysis of its mosaic structural genes. Sci Rep 8, 8086 (2018). https://doi.org/10.1038/s41598-018-26004-4 (Year: 2018).*

Cieplak T, et al. A bacteriophage cocktail targeting *Escherichia coli* reduces *E. coli* in simulated gut conditions, while preserving a non-targeted representative commensal normal microbiota. Gut Microbes. 2018;9(5):391-399. doi: 10.1080/19490976.2018.1447291. Epub Aug. 24, 2018. PMID: 29517960. (Year: 2018).*

Henderson IR, Navarro-Garcia F, Desvaux M, Fernandez RC, Ala'Aldeen D. Type V protein secretion pathway: the autotransporter story. Microbiol Mol Biol Rev. Dec. 2004;68(4):692-744. doi: 10.1128/MMBR.68.4.692-744.2004. PMID: 15590781; PMCID: PMC539010. (Year: 2004).*

Oechslin F. Resistance Development to Bacteriophages Occurring during Bacteriophage Therapy. Viruses. Jun. 30, 2018;10(7):351. doi: 10.3390/v10070351. PMID: 29966329; PMCID: PMC6070868. (Year: 2018).*

International Search Report & Written Opinion issued Jul. 22, 2020 in PCT/IB2019/001262 filed on Nov. 27, 2018, 8 Pages.

Mizoguchi et al. "Coevolution of Bacteriophage PP01 and *Escherichia coli* O157.H7 in Continuous Culture", Applied and Environmental Microbiology, vol. 69, No. 1, 2003, pp. 170-176.

Li et al. "Screening of Polyvalent Phage-Resistant *Escherichia coli* Strains Based on Phage Receptor Analysis", Frontiers in Microbiology. vol. 10, 2019, 14 Pages.

Chatterjee et al. "Interaction of Bacteriophage Lambda with Its *E. coli* Receptor, LamB", Viruses, vol. 4, 2012, pp. 3162-3178.

Wang, Shaohua, Isolation of Lactobacillus Bacteriophages, Functional Gene Expression and Selection of Anti-Bacteriophage Strains. Chinese Faultshaw, Full Database (Electronic Journal) Basic Science Series of the Premium PhD thesis, No. 8, pp. 1-152, pub. Aug. 15, 2010.

Wang, Shaohua et al. Identification and characterization of the two-component cell lysis cassette encoded by temperate bacteriophage φPYB5 of Lactobacillus fermentum. Journal of Applied Microbiology. vol. 105, pp. 1939-1944, 2009, doi: 10.1111/j.1365-2672.2008.03953.x.

Wang, Shaohua et al. Isolation and characterization of a novel virulent phage (phiLdb) of Lactobacillus delbrueckii. International Journal of Food Microbiology. vol. 137, pp. 22-27, 2009, doi: 10.1016/j.ijfoodmicro.2009.10.024.

Extended European Search Report & Opinion issued Dec. 7, 2023 in PCT/IB2019/001262 filed on Nov. 27, 2019.

Los, Marcin et al. Minimization and prevention of phage infections in bioprocesses. Methods in Molecular Biology (Clifton, N.J.), vol. 834, pp. 305-315, 2012, doi:10.1007/978-1-61779-483-4_19.

Wright Rosanna C.T. et al. Resistance evolution against phage combinations depends on the timing and order of exposure. MBIO, vol. 10, No. 5, Oct. 29, 2019, doi: 10.1128/mBio.01652-19. PMID: 31551330; PMCID: PMC6759759.

Japanese Search Report. Issued Oct. 27, 2023 by the Japanese Patent Office in Japanese Patent Application No. 2022-525452.

Japanese Decision to Grant a Patent. Issued Jul. 29, 2024 by the Japanese Patent Office in Japanese Patent Application No. 2022-525452.

* cited by examiner

*E. coli* LCT-BF-01

*E. coli K-12* wild type

Figure. 3

Alignment tfaD (aminoacid change A -> T)

>TfaD Protein alignment Alignment of 2 sequences: TfaD wildtype, TfaD mutated

Score = 757.0, Identities = 145/146 (99%), Positives = 145/146 (99%), Gaps = 0/146 (0%)

```
TfaD wildtype        1 IPAGFVAVFNSDESSWHLVEDHRGKTVYDVASGDALFISELGPLPENVTWLSPEGEFQK
W  60
Consensus              IPAGFVAVFNSDESSWHLVEDHRGKTVYDVASGDALFISELGPLPENVTWLSPEGEFQK
W
TfaD mutated         1 IPAGFVAVFNSDESSWHLVEDHRGKTVYDVASGDALFISELGPLPENVTWLSPEGEFQK
W  60

TfaD wildtype       61 NGTAWVKDAEAEKLFRIREAEETKNSLMQVASEHIAPLQDAVDLEIATEEETSLLEAWK
K 120
Consensus              NGTAWVKD EAEKLFRIREAEETKNSLMQVASEHIAPLQDAVDLEIATEEETSLLEAWK
K
TfaD mutated        61 NGTAWVKDTEAEKLFRIREAEETKNSLMQVASEHIAPLQDAVDLEIATEEETSLLEAWK
K 120

TfaD wildtype      121 YRVLLNRVDTSTAPDIEWPTNPVRE* 146
Consensus              YRVLLNRVDTSTAPDIEWPTNPVRE*
TfaD mutated       121 YRVLLNRVDTSTAPDIEWPTNPVRE* 146
```

Figure. 4

>TfaD Nucleotide alignment Alignment of 2 sequences: TfaD wildtype, TfaD mutated Score = 2063.764, Identities = 429/438 (97%), Positives = 429/438 (97%), Gaps = 0/438 (0%)

```
TfaD wildtype       1 ATTCCAGCTGGCTTCGTGGCTGTTTTCAACAGTGATGAGTCATCGTGGCATCTCGTTGA
A  60
Consensus             ATTCCAGCTGGCTTCGTGGCTGTTTTCAACAGTGATGAGTCATCGTGGCATCTCGTTGA
A
TfaD mutated        1 ATTCCAGCTGGCTTCGTGGCTGTTTTCAACAGTGATGAGTCATCGTGGCATCTCGTTGA
A  60

TfaD wildtype      61 GATCATCGGGGTAAAACGGTTTATGACGTAGCGTCAGGGGACGCGTTATTTATTTCTGA
A 120
Consensus             GATCATCGGGGTAAAACGGTTTATGACGT GC TC GG GACGCGTTATTTATTTCTGA
A
TfaD mutated       61 GATCATCGGGGTAAAACGGTTTATGACGTGGCTTCCGGCGACGCGTTATTTATTTCTGA
A 120

TfaD wildtype     121 CTCGGTCCGTTACCGGAAAATGTTACCTGGTTATCGCCGGAAGGGGAGTTTCAGAAGTG
G 180
Consensus             CTCGGTCCGTTACCGGAAAATGTTACCTGGTTATCGCCGGAAGGGGAGTTTCAGAAGTG
G
TfaD mutated      121 CTCGGTCCGTTACCGGAAAATGTTACCTGGTTATCGCCGGAAGGGGAGTTTCAGAAGTG
G 180

TfaD wildtype     181 AACGGTACAGCCTGGGTGAAAGATGCAGAAGCAGAAAAACTGTTCCGGATTCGGGAGGC
G 240
Consensus             AACGG ACAGCCTGGGTGAA GAT C GAAGCAGAAAAACTGTTCCGGAT CGGGAGGC
G
TfaD mutated      181 AACGGCACAGCCTGGGTGAAGGATACGGAAGCAGAAAAACTGTTCCGGATCCGGGAGGC
G 240

TfaD wildtype     241 GAAGAAACAAAAAACAGCCTGATGCAGGTAGCCAGTGAGCATATTGCGCCACTTCAGGA
T 300
Consensus             GAAGAAACAAAAAACAGCCTGATGCAGGTAGCCAGTGAGCATATTGCGCCACTTCAGGA
T
TfaD mutated      241 GAAGAAACAAAAAACAGCCTGATGCAGGTAGCCAGTGAGCATATTGCGCCACTTCAGGA
T 300

TfaD wildtype     301 GCTGTAGATCTGGAAATCGCAACGGAGGAAGAAACCTCATTGCTGGAAGCCTGGAAAAA
A 360
Consensus             GCTGTAGATCTGGAAATCGCAACGGAGGAAGAAACCTCATTGCTGGAAGCCTGGAAAAA
A
TfaD mutated      301 GCTGTAGATCTGGAAATCGCAACGGAGGAAGAAACCTCATTGCTGGAAGCCTGGAAAAA
A 360

TfaD wildtype     361 TATCGGGTGTTGCTGAACCGTGTTGATACATCAACTGCACCTGATATTGAGTGGCCTAC
G 420
Consensus             TATCGGGTGTTGCTGAACCGTGTTGATACATCAACTGCACCTGATATTGAGTGGCCTAC
G
TfaD mutated      361 TATCGGGTGTTGCTGAACCGTGTTGATACATCAACTGCACCTGATATTGAGTGGCCTAC
G 420

TfaD wildtype     421 AACCCTGTCAGGGAGTAA 438
Consensus             AACCCTGTCAGGGAGTAA
TfaD mutated      421 AACCCTGTCAGGGAGTAA 438
```

Figure. 5A

Alignment yejO (aminoacid change W -> R)

>yejO Protein alignment Alignment of 2 sequences: yejO wildtype, yejO mutated

Score = 6358.0, Identities = 1262/1263 (99%), Positives = 1262/1263 (99%), Gaps = 0/1263 (0%)

```
yejO wildtype      1 MHQSGSVSLCRSAISVLVATALWKVRTSP*YEIMFVIWSHRTGFIMSHQLTFADSEF
SSK    60
Consensus            MHQSGSVSLCRSAISVLVATAL KVRTSP*YEIMFVIWSHRTGFIMSHQLTFADSEF
SSK
yejO mutated       1 MHQSGSVSLCRSAISVLVATALRKVRTSP*YEIMFVIWSHRTGFIMSHQLTFADSEF
SSK    60

yejO wildtype     61 RRQTRKEIFLSRMEQILPWQNMVEVIEPFYPKAGNGRRPYPLETMLRIHCMQHWYNL
SDG   120
Consensus            RRQTRKEIFLSRMEQILPWQNMVEVIEPFYPKAGNGRRPYPLETMLRIHCMQHWYNL
SDG
yejO mutated      61 RRQTRKEIFLSRMEQILPWQNMVEVIEPFYPKAGNGRRPYPLETMLRIHCMQHWYNL
SDG   120

yejO wildtype    121 AMEDALYEIASMRLFARLSLDSALPDRTTIMNFRHLLEQHQLARQLFKTINRWLAEA
GVM   180
Consensus            AMEDALYEIASMRLFARLSLDSALPDRTTIMNFRHLLEQHQLARQLFKTINRWLAEA
GVM
yejO mutated     121 AMEDALYEIASMRLFARLSLDSALPDRTTIMNFRHLLEQHQLARQLFKTINRWLAEA
GVM   180

yejO wildtype    181 MTQGTLVDATIIEAPSSTKNKEQQRDPEMHQTKKGNQWHFGMKAHIGVDAKSGLTHS
LVT   240
Consensus            MTQGTLVDATIIEAPSSTKNKEQQRDPEMHQTKKGNQWHFGMKAHIGVDAKSGLTHS
LVT
yejO mutated     181 MTQGTLVDATIIEAPSSTKNKEQQRDPEMHQTKKGNQWHFGMKAHIGVDAKSGLTHS
LVT   240

yejO wildtype    241 TAANEHDLNQLGNLLHGEEQFVSADAGYQGAPQREELAEVDVDWLIAERPGKVRTLK
QHP   300
Consensus            TAANEHDLNQLGNLLHGEEQFVSADAGYQGAPQREELAEVDVDWLIAERPGKVRTLK
QHP
yejO mutated     241 TAANEHDLNQLGNLLHGEEQFVSADAGYQGAPQREELAEVDVDWLIAERPGKVRTLK
QHP   300

yejO wildtype    301 RKNKTAINIEYMKASIRARVEHPFRIIKRQFGFVKARYKGLLKNDNQLAMLFTLANL
FRA   360
Consensus            RKNKTAINIEYMKASIRARVEHPFRIIKRQFGFVKARYKGLLKNDNQLAMLFTLANL
FRA
yejO mutated     301 RKNKTAINIEYMKASIRARVEHPFRIIKRQFGFVKARYKGLLKNDNQLAMLFTLANL
FRA   360

yejO wildtype    361 DQMIRQWERSH*KLGITP*MAKKRSK*ADSRHLREKKSAQT*RNEMTESAEKNFPAY
SHL   420
Consensus            DQMIRQWERSH*KLGITP*MAKKRSK*ADSRHLREKKSAQT*RNEMTESAEKNFPAY
SHL
yejO mutated     361 DQMIRQWERSH*KLGITP*MAKKRSK*ADSRHLREKKSAQT*RNEMTESAEKNFPAY
SHL   420

yejO wildtype    421 PYIHP*HWHQLLSMVRQLMVLSWKKISSWFMGPPIIRKSILAENSI*KNLV*VIILK
LTE   480
Consensus            PYIHP*HWHQLLSMVRQLMVLSWKKISSWFMGPPIIRKSILAENSI*KNLV*VIILK
LTE
yejO mutated     421 PYIHP*HWHQLLSMVRQLMVLSWKKISSWFMGPPIIRKSILAENSI*KNLV*VIILK
LTE   480

yejO wildtype    481 GISTLK*MAPQNTQY*MTVIKLFKWVARQTRLRSIMVCYRFMAQRMIPRLKAGA*SL
```

Figure 5B

```
KKM   540
Consensus                    GISTLK*MAPQNTQY*MTVIKLFKWVARQTRLRSIMVCYRFMAQRMIPRLKAGA*SL
KKM
yejO mutated           481   GISTLK*MAPQNTQY*MTVIKLFKWVARQTRLRSIMVCYRFMAQRMIPRLKAGA*SL
KKM   540

yejO wildtype          541   GGPSLSLSKREDYWRLKRGDLHLR*IRKQAVLLKQPRGPWRYSEQTVSVSSISRMVL
LII   600
Consensus                    GGPSLSLSKREDYWRLKRGDLHLR*IRKQAVLLKQPRGPWRYSEQTVSVSSISRMVL
LII
yejO mutated           541   GGPSLSLSKREDYWRLKRGDLHLR*IRKQAVLLKQPRGPWRYSEQTVSVSSISRMVL
LII   600

yejO wildtype          601   CCWKTAEVCELKKMTSLIIPL*IVAAYWRLWMAGL*LALIKKQAEN*LSQRMRWK*V
VQT   660
Consensus                    CCWKTAEVCELKKMTSLIIPL*IVAAYWRLWMAGL*LALIKKQAEN*LSQRMRWK*V
VQT
yejO mutated           601   CCWKTAEVCELKKMTSLIIPL*IVAAYWRLWMAGL*LALIKKQAEN*LSQRMRWK*V
VQT   660

yejO wildtype          661   VKANLV*KMVCQKIMNWMMVPGSLLWRTRRPLILSLISMPLCNRWERILVRKCRQMR
YMI   720
Consensus                    VKANLV*KMVCQKIMNWMMVPGSLLWRTRRPLILSLISMPLCNRWERILVRKCRQMR
YMI
yejO mutated           661   VKANLV*KMVCQKIMNWMMVPGSLLWRTRRPLILSLISMPLCNRWERILVRKCRQMR
YMI   720

yejO wildtype          721   SVDHIRMEVSRIPQKPSLKIWLSTMAALTSGLAQWLTFQSEGMMAFLRS*SRK*IMH
PQC   780
Consensus                    SVDHIRMEVSRIPQKPSLKIWLSTMAALTSGLAQWLTFQSEGMMAFLRS*SRK*IMH
PQC
yejO mutated           721   SVDHIRMEVSRIPQKPSLKIWLSTMAALTSGLAQWLTFQSEGMMAFLRS*SRK*IMH
PQC   780

yejO wildtype          781   WWVR*WFLRALLLERMVPWIPAKRTFRSKIAYGPSLPISLRRTKTPSST*PTLRCLT
QM*   840
Consensus                    WWVR*WFLRALLLERMVPWIPAKRTFRSKIAYGPSLPISLRRTKTPSST*PTLRCLT
QM*
yejO mutated           781   WWVR*WFLRALLLERMVPWIPAKRTFRSKIAYGPSLPISLRRTKTPSST*PTLRCLT
QM*   840

yejO wildtype          841   L*WMSQ*LVHQ*RQVRKISLR*PPIPCRETAIFICVPIWLIIRAISSTSPVRQQVIS
KYS   900
Consensus                    L*WMSQ*LVHQ*RQVRKISLR*PPIPCRETAIFICVPIWLIIRAISSTSPVRQQVIS
KYS
yejO mutated           841   L*WMSQ*LVHQ*RQVRKISLR*PPIPCRETAIFICVPIWLIIRAISSTSPVRQQVIS
KYS   900

yejO wildtype          901   *RTPVPARQQEIALHW*QRAAVMLHLRWAMPEALLISVRMNIPCWIMATIAGVWQRI
ARK   960
Consensus                    *RTPVPARQQEIALHW*QRAAVMLHLRWAMPEALLISVRMNIPCWIMATIAGVWQRI
ARK
yejO mutated           901   *RTPVPARQQEIALHW*QRAAVMLHLRWAMPEALLISVRMNIPCWIMATIAGVWQRI
ARK   960

yejO wildtype          961   LPLQPLMC*IWRPHNRWYLMQNWTPCVSVLVA*KALVTIRRCGVRQLTPATT*PLMR
ELV  1020
Consensus                    LPLQPLMC*IWRPHNRWYLMQNWTPCVSVLVA*KALVTIRRCGVRQLTPATT*PLMR
ELV
yejO mutated           961   LPLQPLMC*IWRPHNRWYLMQNWTPCVSVLVA*KALVTIRRCGVRQLTPATT*PLMR
ELV  1020

yejO wildtype         1021   LSKH*RA*RSVSIAVSPVKKAVQFAA*SLVTLILILVLIAAAKVISIAIPWGLMPVG
SIR  1080
Consensus                    LSKH*RA*RSVSIAVSPVKKAVQFAA*SLVTLILILVLIAAAKVISIAIPWGLMPVG
SIR
yejO mutated          1021   LSKH*RA*RSVSIAVSPVKKAVQFAA*SLVTLILILVLIAAAKVISIAIPWGLMPVG
SIR  1080

yejO wildtype         1081   TVPMLMGW*KLTVLPTPSMAR*VMGQQRLAITIVTARVLMLRAGSVGLTDCGVLDPI
WPL  1140
Consensus                    TVPMLMGW*KLTVLPTPSMAR*VMGQQRLAITIVTARVLMLRAGSVGLTDCGVLDPI
```

Figure 5C

```
WPL
yejO mutated        1061 TVPMLMGW*KLTVLPTPSMAR*VMGQQRLAITIVTARVLMLRAGSVGLTDCGVLDPI
WPL 1140

yejO wildtype       1141 PALPQMVRTTRYQTACARMWEIPGYYALKRERR*AITWTCKTVRRWNPG*KRPCVRN
TPI 1200
Consensus                PALPQMVRTTRYQTACARMWEIPGYYALKRERR*AITWTCKTVRRWNPG*KRPCVRN
TPI
yejO mutated        1141 PALPQMVRTTRYQTACARMWEIPGYYALKRERR*AITWTCKTVRRWNPG*KRPCVRN
TPI 1200

yejO wildtype       1201 LTR*KLMTMANLIMMWLEPVAFIRLV*GHRLPRR*AVICQSAMAMAQG*NRRGILRR
VWS 1260
Consensus                LTR*KLMTMANLIMMWLEPVAFIRLV*GHRLPRR*AVICQSAMAMAQG*NRRGILRR
VWS
yejO mutated        1201 LTR*KLMTMANLIMMWLEPVAFIRLV*GHRLPRR*AVICQSAMAMAQG*NRRGILRR
VWS 1260

yejO wildtype       1261 GRS 1263
Consensus                GRS
yejO mutated        1261 GRS 1263
```

Figure. 6A

>yejO Nucleotide alignment Alignment of 2 sequences: yejO wildtype, yejO mutated Score = 18940.974, Identities = 3790/3791 (99%), Positives = 3790/3791 (99%), Gaps = 0/3791 (0%)

```
yejO wildtype        1 ATGCATCAATCTGGTTCTGTTTCTCTTTGTCGTTCCGCAATATCTGTTCTGGTGGCTA
CA    60
Consensus              ATGCATCAATCTGGTTCTGTTTCTCTTTGTCGTTCCGCAATATCTGTTCTGGTGGCTA
CA
yejO mutated         1 ATGCATCAATCTGGTTCTGTTTCTCTTTGTCGTTCCGCAATATCTGTTCTGGTGGCTA
CA    60

yejO wildtype       61 GCGTTA[illegible]GGAAGGTGCGAACAAGTCCCTGATATGAGATCATGTTTGTCATCTGGAGCC
AT   120
Consensus              GCGTTA GGAAGGTGCGAACAAGTCCCTGATATGAGATCATGTTTGTCATCTGGAGCC
AT
yejO mutated        61 GCGTTAAGGAAGGTGCGAACAAGTCCCTGATATGAGATCATGTTTGTCATCTGGAGCC
AT   120

yejO wildtype      121 AGAACAGGGTTCATCATGAGTCATCAACTTACCTTCGCCGACAGTGAATTCAGCAGTA
AG   180
Consensus              AGAACAGGGTTCATCATGAGTCATCAACTTACCTTCGCCGACAGTGAATTCAGCAGTA
AG
yejO mutated       121 AGAACAGGGTTCATCATGAGTCATCAACTTACCTTCGCCGACAGTGAATTCAGCAGTA
AG   180

yejO wildtype      181 CGCCGTCAGACCAGAAAAGAGATTTTCTTGTCCCGCATGGAGCAGATTCTGCCATGGC
AA   240
Consensus              CGCCGTCAGACCAGAAAAGAGATTTTCTTGTCCCGCATGGAGCAGATTCTGCCATGGC
AA
yejO mutated       181 CGCCGTCAGACCAGAAAAGAGATTTTCTTGTCCCGCATGGAGCAGATTCTGCCATGGC
AA   240

yejO wildtype      241 AACATGGTGGAAGTCATCGAGCCGTTTTACCCCAAGGCTGGTAATGGCCGGCGACCTT
AT   300
Consensus              AACATGGTGGAAGTCATCGAGCCGTTTTACCCCAAGGCTGGTAATGGCCGGCGACCTT
AT
yejO mutated       241 AACATGGTGGAAGTCATCGAGCCGTTTTACCCCAAGGCTGGTAATGGCCGGCGACCTT
AT   300

yejO wildtype      301 CCGCTGGAAACCATGCTACGCATTCACTGCATGCAGCATTGGTACAACCTGAGCGATG
GC   360
Consensus              CCGCTGGAAACCATGCTACGCATTCACTGCATGCAGCATTGGTACAACCTGAGCGATGG
C
yejO mutated       301 CCGCTGGAAACCATGCTACGCATTCACTGCATGCAGCATTGGTACAACCTGAGCGATG
GC   360

yejO wildtype      361 GCGATGGAAGATGCTCTGTACGAAATCGCCTCCATGCGTCTGTTTGCCCGGTTATCCC
TG   420
Consensus              GCGATGGAAGATGCTCTGTACGAAATCGCCTCCATGCGTCTGTTTGCCCGGTTATCCC
TG
yejO mutated       361 GCGATGGAAGATGCTCTGTACGAAATCGCCTCCATGCGTCTGTTTGCCCGGTTATCCC
TG   420

yejO wildtype      421 GATAGCGCCTTGCCGGACCGCACCACCATCATGAATTTCCGCCACCTGCTGGAGCAGC
AT   480
Consensus              GATAGCGCCTTGCCGGACCGCACCACCATCATGAATTTCCGCCACCTGCTGGAGCAGC
AT
yejO mutated       421 GATAGCGCCTTGCCGGACCGCACCACCATCATGAATTTCCGCCACCTGCTGGAGCAGC
AT   480

yejO wildtype      481 CAACTGGCCCGCCAATTGTTCAAGACCATCAATCGCTGGCTGGCCGAAGCAGGCGTCA
TG   540
Consensus              CAACTGGCCCGCCAATTGTTCAAGACCATCAATCGCTGGCTGGCCGAAGCAGGCGTCA
TG
yejO mutated       481 CAACTGGCCCGCCAATTGTTCAAGACCATCAATCGCTGGCTGGCCGAAGCAGGCGTCA
```

Figure 6B

```
TG  540

yejO wildtype      541 ATGACTCAAGGCACCTTGGTCGATGCCACCATCATTGAGGCACCCAGCTCGACCAAGA
AC  600
Consensus              ATGACTCAAGGCACCTTGGTCGATGCCACCATCATTGAGGCACCCAGCTCGACCAAGA
AC
yejO mutated       541 ATGACTCAAGGCACCTTGGTCGATGCCACCATCATTGAGGCACCCAGCTCGACCAAGA
AC  600

yejO wildtype      601 AAAGAGCAGCAACGCGATCCGGAGATGCATCAGACCAAGAAAGGCAATCAGTGGCACT
TT  660
Consensus              AAAGAGCAGCAACGCGATCCGGAGATGCATCAGACCAAGAAAGGCAATCAGTGGCACT
TT
yejO mutated       601 AAAGAGCAGCAACGCGATCCGGAGATGCATCAGACCAAGAAAGGCAATCAGTGGCACT
TT  660

yejO wildtype      661 GGCATGAAGGCCCACATTGGTGTCGATGCCAAGAGTGGCCTGACCCACAGCCTGGTCA
CC  720
Consensus              GGCATGAAGGCCCACATTGGTGTCGATGCCAAGAGTGGCCTGACCCACAGCCTGGTCA
CC
yejO mutated       661 GGCATGAAGGCCCACATTGGTGTCGATGCCAAGAGTGGCCTGACCCACAGCCTGGTCA
CC  720

yejO wildtype      721 ACCGCGGCCAACGAGCATGACCTCAATCAGCTGGGTAATCTGCTGCATGGAGAGGAGC
AA  780
Consensus              ACCGCGGCCAACGAGCATGACCTCAATCAGCTGGGTAATCTGCTGCATGGAGAGGAGC
AA
yejO mutated       721 ACCGCGGCCAACGAGCATGACCTCAATCAGCTGGGTAATCTGCTGCATGGAGAGGAGC
AA  780

yejO wildtype      781 TTTGTCTCAGCCGATGCCGGCTACCAAGGGGCGCCACAGCGCGAGGAGCTGGCCGAGG
TG  840
Consensus              TTTGTCTCAGCCGATGCCGGCTACCAAGGGGCGCCACAGCGCGAGGAGCTGGCCGAGG
TG
yejO mutated       781 TTTGTCTCAGCCGATGCCGGCTACCAAGGGGCGCCACAGCGCGAGGAGCTGGCCGAGG
TG  840

yejO wildtype      841 GATGTGGACTGGCTGATCGCCGAGCGCCCCGGCAAGGTAAGAACCTTGAAACAGCATC
CA  900
Consensus              GATGTGGACTGGCTGATCGCCGAGCGCCCCGGCAAGGTAAGAACCTTGAAACAGCATC
CA
yejO mutated       841 GATGTGGACTGGCTGATCGCCGAGCGCCCCGGCAAGGTAAGAACCTTGAAACAGCATC
CA  900

yejO wildtype      901 CGCAAGAACAAAACGGCCATCAACATCGAATACATGAAAGCCAGCATCCGGGCCAGGG
TG  960
Consensus              CGCAAGAACAAAACGGCCATCAACATCGAATACATGAAAGCCAGCATCCGGGCCAGGG
TG
yejO mutated       901 CGCAAGAACAAAACGGCCATCAACATCGAATACATGAAAGCCAGCATCCGGGCCAGGG
TG  960

yejO wildtype      961 GAGCACCCATTTCGCATCATCAAGCGACAGTTCGGCTTCGTGAAAGCCAGATACAAGG
GG 1020
Consensus              GAGCACCCATTTCGCATCATCAAGCGACAGTTCGGCTTCGTGAAAGCCAGATACAAGG
GG
yejO mutated       961 GAGCACCCATTTCGCATCATCAAGCGACAGTTCGGCTTCGTGAAAGCCAGATACAAGG
GG 1020

yejO wildtype     1021 TTGCTGAAAAACGATAACCAACTGGCGATGTTATTCACGCTGGCCAACCTGTTTCGGG
CG 1080
Consensus              TTGCTGAAAAACGATAACCAACTGGCGATGTTATTCACGCTGGCCAACCTGTTTCGGG
CG
yejO mutated      1021 TTGCTGAAAAACGATAACCAACTGGCGATGTTATTCACGCTGGCCAACCTGTTTCGGG
CG 1080

yejO wildtype     1081 GACCAAATGATACGTCAGTGGGAGAGATCTCACTAAAAACTGGGGATAACGCCTTAAA
TG 1140
Consensus              GACCAAATGATACGTCAGTGGGAGAGATCTCACTAAAAACTGGGGATAACGCCTTAAA
TG
yejO mutated      1081 GACCAAATGATACGTCAGTGGGAGAGATCTCACTAAAAACTGGGGATAACGCCTTAAA
TG 1140
```

Figure 6C yejO wildtype 1141 GCGAAGAAACGGTCTAAATAGGCTGATTCAAGGCATTTACGGGAGAAAAAATCGGCTC
AA 1200
Consensus GCGAAGAAACGGTCTAAATAGGCTGATTCAAGGCATTTACGGGAGAAAAAATCGGCTC
AA
yejO mutated 1141 GCGAAGAAACGGTCTAAATAGGCTGATTCAAGGCATTTACGGGAGAAAAAATCGGCTC
AA 1200 yejO wildtype 1201 ACATGAAGAAATGAAATGACTGAGTCAGCCGAGAAGAATTTCCCCGCTTATTCGCACC
TT 1260
Consensus ACATGAAGAAATGAAATGACTGAGTCAGCCGAGAAGAATTTCCCCGCTTATTCGCACC
TT
yejO mutated 1201 ACATGAAGAAATGAAATGACTGAGTCAGCCGAGAAGAATTTCCCCGCTTATTCGCACC
TT 1260 yejO wildtype 1261 CCTTATATTCACCCATAGCATTGGCATCAACTGTTGAGTATGGTGAGACAGTTGATGG
TG 1320
Consensus CCTTATATTCACCCATAGCATTGGCATCAACTGTTGAGTATGGTGAGACAGTTGATGG
TG
yejO mutated 1261 CCTTATATTCACCCATAGCATTGGCATCAACTGTTGAGTATGGTGAGACAGTTGATGG
TG 1320 yejO wildtype 1321 TTGTCCTGGAAAAAGATATCCAGCTGGTTTATGGGACCGCCAATAATACGAAAATCAA
TC 1380
Consensus TTGTCCTGGAAAAAGATATCCAGCTGGTTTATGGGACCGCCAATAATACGAAAATCAA
TC
yejO mutated 1321 TTGTCCTGGAAAAAGATATCCAGCTGGTTTATGGGACCGCCAATAATACGAAAATCAA
TC 1380 yejO wildtype 1381 CTGGCGGAGAACAGCATATAAAAGAATTTGGTGTAAGTAATAATACTGAAATTAACGG
AG 1440
Consensus CTGGCGGAGAACAGCATATAAAAGAATTTGGTGTAAGTAATAATACTGAAATTAACGG
AG
yejO mutated 1381 CTGGCGGAGAACAGCATATAAAAGAATTTGGTGTAAGTAATAATACTGAAATTAACGG
AG 1440 yejO wildtype 1441 GGTATCAGTACATTGAAATGAATGGCGCCGCAGAATACTCAGTATTAAATGACGGTTA
TC 1500
Consensus GGTATCAGTACATTGAAATGAATGGCGCCGCAGAATACTCAGTATTAAATGACGGTTA
TC
yejO mutated 1441 GGTATCAGTACATTGAAATGAATGGCGCCGCAGAATACTCAGTATTAAATGACGGTTA
TC 1500 yejO wildtype 1501 AAATTGTTCAAATGGGTGGCGCGGCAAACCAGACTACGCTCAATAATGGTGTGCTACA
GG 1560
Consensus AAATTGTTCAAATGGGTGGCGCGGCAAACCAGACTACGCTCAATAATGGTGTGCTACA
GG
yejO mutated 1501 AAATTGTTCAAATGGGTGGCGCGGCAAACCAGACTACGCTCAATAATGGTGTGCTACA
GG 1560 yejO wildtype 1561 TTTATGGCGCAGCGAATGATACCACGATTAAAGGCGGGCGCTTAATCGTTGAAAAAGA
TG 1620
Consensus TTTATGGCGCAGCGAATGATACCACGATTAAAGGCGGGCGCTTAATCGTTGAAAAAGA
TG
yejO mutated 1561 TTTATGGCGCAGCGAATGATACCACGATTAAAGGCGGGCGCTTAATCGTTGAAAAAGA
TG 1620 yejO wildtype 1621 GGGGGGCCGTCTTTGTCGCTATCGAAAAGGGAGGACTACTGGAGGTTAAAGAGGGGGG
AT 1680
Consensus GGGGGGCCGTCTTTGTCGCTATCGAAAAGGGAGGACTACTGGAGGTTAAAGAGGGGGG
AT
yejO mutated 1621 GGGGGGCCGTCTTTGTCGCTATCGAAAAGGGAGGACTACTGGAGGTTAAAGAGGGGGG
AT 1680 yejO wildtype 1681 TTGCATTTGCGGTAGATCAGAAAGCAGGCGGTGCTATTAAAACAACCACGCGGGCCAT
GG 1740
Consensus TTGCATTTGCGGTAGATCAGAAAGCAGGCGGTGCTATTAAAACAACCACGCGGGCCAT
GG
yejO mutated 1681 TTGCATTTGCGGTAGATCAGAAAGCAGGCGGTGCTATTAAAACAACCACGCGGGCCAT
GG 1740 yejO wildtype 1741 AGGTATTCGGAACAAACCGTCTCGGTCAGTTCGATATCAAGAATGGTATTGCTAATAA
TA 1800

Figure 6D

```
Consensus                  AGGTATTCGGAACAAACCGTCTCGGTCAGTTCGATATCAAGAATGGTATTGCTAATAA
TA
yejO mutated         1741  AGGTATTCGGAACAAACCGTCTCGGTCAGTTCGATATCAAGAATGGTATTGCTAATAA
TA 1800

yejO wildtype        1801  TGTTGTTGGAAAACGGCGGAAGTTTGCGAGTTGAAGAAAATGACTTCGCTTATAATAC
CA 1860
Consensus                  TGTTGTTGGAAAACGGCGGAAGTTTGCGAGTTGAAGAAAATGACTTCGCTTATAATAC
CA
yejO mutated         1801  TGTTGTTGGAAAACGGCGGAAGTTTGCGAGTTGAAGAAAATGACTTCGCTTATAATAC
CA 1860

yejO wildtype        1861  CTGTAGATAGTGGCGGCTTACTGGAGGTTATGGATGGCGGGACTGTAACTGGCGTTGA
TA 1920
Consensus                  CTGTAGATAGTGGCGGCTTACTGGAGGTTATGGATGGCGGGACTGTAACTGGCGTTGA
TA
yejO mutated         1861  CTGTAGATAGTGGCGGCTTACTGGAGGTTATGGATGGCGGGACTGTAACTGGCGTTGA
TA 1920

yejO wildtype        1921  AAAAAGCAGGCGGAAAATTAATTGTCTCAACGAATGCGCTGGAAGTGAGTGGTCCAAA
CA 1980
Consensus                  AAAAAGCAGGCGGAAAATTAATTGTCTCAACGAATGCGCTGGAAGTGAGTGGTCCAAA
CA
yejO mutated         1921  AAAAAGCAGGCGGAAAATTAATTGTCTCAACGAATGCGCTGGAAGTGAGTGGTCCAAA
CA 1980

yejO wildtype        1981  GTAAAGGCCAATTTAGTATAAAAGATGGTGTGTCAAAAAATTATGAACTGGATGATGG
TT 2040
Consensus                  GTAAAGGCCAATTTAGTATAAAAGATGGTGTGTCAAAAAATTATGAACTGGATGATGG
TT
yejO mutated         1981  GTAAAGGCCAATTTAGTATAAAAGATGGTGTGTCAAAAAATTATGAACTGGATGATGG
TT 2040

yejO wildtype        2041  CCGGGCTCATTGTTATGGAGGACACGCAGGCCATTGATACTATCCTTGATAAGCATGC
CA 2100
Consensus                  CCGGGCTCATTGTTATGGAGGACACGCAGGCCATTGATACTATCCTTGATAAGCATGC
CA
yejO mutated         2041  CCGGGCTCATTGTTATGGAGGACACGCAGGCCATTGATACTATCCTTGATAAGCATGC
CA 2100

yejO wildtype        2101  CTATGCAATCGCTGGGAAAGGATACTGGTACGAAAGTGCAGGCAAATGCGGTATATGA
TC 2160
Consensus                  CTATGCAATCGCTGGGAAAGGATACTGGTACGAAAGTGCAGGCAAATGCGGTATATGA
TC
yejO mutated         2101  CTATGCAATCGCTGGGAAAGGATACTGGTACGAAAGTGCAGGCAAATGCGGTATATGA
TC 2160

yejO wildtype        2161  TCGGTCGATCATATCAGAATGGAAGTATCACGTATTCCTCAAAAGCCATCTCTGAAAA
TA 2220
Consensus                  TCGGTCGATCATATCAGAATGGAAGTATCACGTATTCCTCAAAAGCCATCTCTGAAAA
TA
yejO mutated         2161  TCGGTCGATCATATCAGAATGGAAGTATCACGTATTCCTCAAAAGCCATCTCTGAAAA
TA 2220

yejO wildtype        2221  TGGTTATCAACAATGGCCGCGCTAACGTCTGGGCTGGCACAATGGTTAACGTTTCAGT
CA 2280
Consensus                  TGGTTATCAACAATGGCCGCGCTAACGTCTGGGCTGGCACAATGGTTAACGTTTCAGT
CA
yejO mutated         2221  TGGTTATCAACAATGGCCGCGCTAACGTCTGGGCTGGCACAATGGTTAACGTTTCAGT
CA 2280

yejO wildtype        2281  GAGGGAATGATGGCATTCTTGAGGTCATGAAGCCGCAAATAAATTATGCACCCGCAAT
GT 2340
Consensus                  GAGGGAATGATGGCATTCTTGAGGTCATGAAGCCGCAAATAAATTATGCACCCGCAAT
GT
yejO mutated         2281  GAGGGAATGATGGCATTCTTGAGGTCATGAAGCCGCAAATAAATTATGCACCCGCAAT
GT 2340

yejO wildtype        2341  TGGTGGGTAAGGTAGTGGTTTCTGAGGGCGCTTCTTTTAGAACGCATGGTGCCGTGGA
TA 2400
Consensus                  TGGTGGGTAAGGTAGTGGTTTCTGAGGGCGCTTCTTTTAGAACGCATGGTGCCGTGGA
TA
```

Figure 6E yejO mutated 2341 TGGTGGGTAAGGTAGTGGTTTCTGAGGGCGCTTCTTTTAGAACGCATGGTGCCGTGGA
TA 2400 yejO wildtype 2401 CCAGCAAAGCGGACGTTTCGCTCGAAAATAGCGTATGGACCATCATTGCCGATATCAC
TA 2460
Consensus CCAGCAAAGCGGACGTTTCGCTCGAAAATAGCGTATGGACCATCATTGCCGATATCAC
TA
yejO mutated 2401 CCAGCAAAGCGGACGTTTCGCTCGAAAATAGCGTATGGACCATCATTGCCGATATCAC
TA 2460 yejO wildtype 2461 CGACGAACCAAAACACCCTCCTCAACTTAGCCAACCTTGCGATGTCTGACGCAAATGT
GA 2520
Consensus CGACGAACCAAAACACCCTCCTCAACTTAGCCAACCTTGCGATGTCTGACGCAAATGT
GA
yejO mutated 2461 CGACGAACCAAAACACCCTCCTCAACTTAGCCAACCTTGCGATGTCTGACGCAAATGT
GA 2520 yejO wildtype 2521 TTATGATGGATGAGCCAGTGACTCGTTCATCAGTGACGGCAAGTGCGGAAAATTTCAT
TA 2580
Consensus TTATGATGGATGAGCCAGTGACTCGTTCATCAGTGACGGCAAGTGCGGAAAATTTCAT
TA
yejO mutated 2521 TTATGATGGATGAGCCAGTGACTCGTTCATCAGTGACGGCAAGTGCGGAAAATTTCAT
TA 2580 yejO wildtype 2581 CGTTGACCACCAATACCCTGTCGGGAAACGGCAATTTTTATATGCGTACCGATATGGC
TA 2640
Consensus CGTTGACCACCAATACCCTGTCGGGAAACGGCAATTTTTATATGCGTACCGATATGGC
TA
yejO mutated 2581 CGTTGACCACCAATACCCTGTCGGGAAACGGCAATTTTTATATGCGTACCGATATGGC
TA 2640 yejO wildtype 2641 ATCATCAGAGCGATCAGCTCAACGTCACCGGTCAGGCAACAGGTGATTTCAAAATATT
CG 2700
Consensus ATCATCAGAGCGATCAGCTCAACGTCACCGGTCAGGCAACAGGTGATTTCAAAATATT
CG
yejO mutated 2641 ATCATCAGAGCGATCAGCTCAACGTCACCGGTCAGGCAACAGGTGATTTCAAAATATT
CG 2700 yejO wildtype 2701 TGACGGACACCGGTGCCAGCCCGGCAGCAGGAGATAGCCTTACACTGGTAACAACGGG
CG 2760
Consensus TGACGGACACCGGTGCCAGCCCGGCAGCAGGAGATAGCCTTACACTGGTAACAACGGG
CG
yejO mutated 2701 TGACGGACACCGGTGCCAGCCCGGCAGCAGGAGATAGCCTTACACTGGTAACAACGGG
CG 2760 yejO wildtype 2761 GCGGTGATGCTGCATTTACGTTGGGCAATGCCGGAGGCGTTGTTGATATCGGTACGTA
TG 2820
Consensus GCGGTGATGCTGCATTTACGTTGGGCAATGCCGGAGGCGTTGTTGATATCGGTACGTA
TG
yejO mutated 2761 GCGGTGATGCTGCATTTACGTTGGGCAATGCCGGAGGCGTTGTTGATATCGGTACGTA
TG 2820 yejO wildtype 2821 AATATACCTTGCTGGATAATGGCAACCATAGCTGGAGTCTGGCAGAGAATCGCGCGCA
AA 2880
Consensus AATATACCTTGCTGGATAATGGCAACCATAGCTGGAGTCTGGCAGAGAATCGCGCGCA
AA
yejO mutated 2821 AATATACCTTGCTGGATAATGGCAACCATAGCTGGAGTCTGGCAGAGAATCGCGCGCA
AA 2880 yejO wildtype 2881 TTACCCCTTCAACCACTGATGTGCTGAATATGGCGGCCGCACAACCGCTGGTATTTGA
TG 2940
Consensus TTACCCCTTCAACCACTGATGTGCTGAATATGGCGGCCGCACAACCGCTGGTATTTGA
TG
yejO mutated 2881 TTACCCCTTCAACCACTGATGTGCTGAATATGGCGGCCGCACAACCGCTGGTATTTGA
TG 2940 yejO wildtype 2941 CAGAACTGGACACCGTGCGTGAGCGTCTTGGTAGCGTAAAAGGCGTTAGTTACGATAC
GG 3000
Consensus CAGAACTGGACACCGTGCGTGAGCGTCTTGGTAGCGTAAAAGGCGTTAGTTACGATAC
GG
yejO mutated 2941 CAGAACTGGACACCGTGCGTGAGCGTCTTGGTAGCGTAAAAGGCGTTAGTTACGATAC
GG 3000

Figure 6F yejO wildtype 3001 CGATGTGGAGTTCGGCAATTAACACCCGCAACAACGTGACCACTGATGCGGGAGCTGG
TT 3060
Consensus CGATGTGGAGTTCGGCAATTAACACCCGCAACAACGTGACCACTGATGCGGGAGCTGG
TT
yejO mutated 3001 CGATGTGGAGTTCGGCAATTAACACCCGCAACAACGTGACCACTGATGCGGGAGCTGG
TT 3060 yejO wildtype 3061 TTGAGCAAACATTGACGGGCCTGACGCTCGGTATCGATAGCCGTTTCTCCCGTGAAGA
AA 3120
Consensus TTGAGCAAACATTGACGGGCCTGACGCTCGGTATCGATAGCCGTTTCTCCCGTGAAGA
AA
yejO mutated 3061 TTGAGCAAACATTGACGGGCCTGACGCTCGGTATCGATAGCCGTTTCTCCCGTGAAGA
AA 3120 yejO wildtype 3121 GCAGTACAATTCGCGGCTTGATCTTTGGTTACTCTCATTCTGATATTGGTTTTGATCG
CG 3180
Consensus GCAGTACAATTCGCGGCTTGATCTTTGGTTACTCTCATTCTGATATTGGTTTTGATCG
CG
yejO mutated 3121 GCAGTACAATTCGCGGCTTGATCTTTGGTTACTCTCATTCTGATATTGGTTTTGATCG
CG 3180 yejO wildtype 3181 GCGGCAAAGGTAATATCGATAGCTATACCCTGGGGGCTTATGCCGGTTGGGAGCATCA
GA 3240
Consensus GCGGCAAAGGTAATATCGATAGCTATACCCTGGGGGCTTATGCCGGTTGGGAGCATCA
GA
yejO mutated 3181 GCGGCAAAGGTAATATCGATAGCTATACCCTGGGGGCTTATGCCGGTTGGGAGCATCA
GA 3240 yejO wildtype 3241 ACGGTGCCTATGTTGATGGGGTGGTGAAAGTTGACCGTTTTGCCAACACCATCCATGG
CA 3300
Consensus ACGGTGCCTATGTTGATGGGGTGGTGAAAGTTGACCGTTTTGCCAACACCATCCATGG
CA
yejO mutated 3241 ACGGTGCCTATGTTGATGGGGTGGTGAAAGTTGACCGTTTTGCCAACACCATCCATGG
CA 3300 yejO wildtype 3301 AGATGAGTAATGGGGCAACAGCGTTTGGCGATTACAATAGTAACGGCGCGGGTGCTCA
TG 3360
Consensus AGATGAGTAATGGGGCAACAGCGTTTGGCGATTACAATAGTAACGGCGCGGGTGCTCA
TG
yejO mutated 3301 AGATGAGTAATGGGGCAACAGCGTTTGGCGATTACAATAGTAACGGCGCGGGTGCTCA
TG 3360 yejO wildtype 3361 TTGAGAGCGGGTTCCGTTGGGTTGACGGATTGTGGAGTGTTAGACCCTATCTGGCCTT
TA 3420
Consensus TTGAGAGCGGGTTCCGTTGGGTTGACGGATTGTGGAGTGTTAGACCCTATCTGGCCTT
TA
yejO mutated 3361 TTGAGAGCGGGTTCCGTTGGGTTGACGGATTGTGGAGTGTTAGACCCTATCTGGCCTT
TA 3420 yejO wildtype 3421 CCGGCTTTACCACAGATGGTCAGGACTACACGTTATCAAACGGCATGCGCGCGGATGT
GG 3480
Consensus CCGGCTTTACCACAGATGGTCAGGACTACACGTTATCAAACGGCATGCGCGCGGATGT
GG
yejO mutated 3421 CCGGCTTTACCACAGATGGTCAGGACTACACGTTATCAAACGGCATGCGCGCGGATGT
GG 3480 yejO wildtype 3481 GAAATACCCGGATATTACGCGCTGAAGCGGGAACGGCGGTAAGCTATCACATGGACCT
GC 3540
Consensus GAAATACCCGGATATTACGCGCTGAAGCGGGAACGGCGGTAAGCTATCACATGGACCT
GC
yejO mutated 3481 GAAATACCCGGATATTACGCGCTGAAGCGGGAACGGCGGTAAGCTATCACATGGACCT
GC 3540 yejO wildtype 3541 AAAACGGTACGACGCTGGAACCCTGGCTGAAAGCGGCCGTGCGTCAGGAATACGCCGA
TT 3600
Consensus AAAACGGTACGACGCTGGAACCCTGGCTGAAAGCGGCCGTGCGTCAGGAATACGCCGA
TT
yejO mutated 3541 AAAACGGTACGACGCTGGAACCCTGGCTGAAAGCGGCCGTGCGTCAGGAATACGCCGA
TT 3600 yejO wildtype 3601 CTAACCAGGTGAAAGTTAATGACGATGGCAAATTTAATAATGATGTGGCTGGAACCAG

Figure 6G

```
TG 3660
Consensus                  CTAACCAGGTGAAAGTTAATGACGATGGCAAATTTAATAATGATGTGGCTGGAACCAG
TG
yejO mutated         3601 CTAACCAGGTGAAAGTTAATGACGATGGCAAATTTAATAATGATGTGGCTGGAACCAG
TG 3660

yejO wildtype        3661 GCGTTTATCAGGCTGGTATAAGGTCATCGTTTACCCCGACGTTAAGCGGTCATTTGTC
AG 3720
Consensus                  GCGTTTATCAGGCTGGTATAAGGTCATCGTTTACCCCGACGTTAAGCGGTCATTTGTC
AG
yejO mutated         3661 GCGTTTATCAGGCTGGTATAAGGTCATCGTTTACCCCGACGTTAAGCGGTCATTTGTC
AG 3720

yejO wildtype        3721 TCAGCTATGGCAATGGCGCAGGGGTAGAATCGCCGTGGAATACTCAGGCGGGTGTGGT
CT 3780
Consensus                  TCAGCTATGGCAATGGCGCAGGGGTAGAATCGCCGTGGAATACTCAGGCGGGTGTGGT
CT
yejO mutated         3721 TCAGCTATGGCAATGGCGCAGGGGTAGAATCGCCGTGGAATACTCAGGCGGGTGTGGT
CT 3780

yejO wildtype        3781 GGACGTTCTGA 3791
Consensus                  GGACGTTCTGA
yejO mutated         3781 GGACGTTCTGA 3791
```

PHAGE-RESISTANT MICROORGANISMS

BACKGROUND OF THE INVENTION

Field of the Invention

The present invention provides genetically modified microorganisms that are resistant to infection by bacteriophages. The present invention also provides a method of making bacteriophage-infection resistant microorganisms.

Description of the Related Art

Bacterial cultures are the center of the biotechnology industry. Whether a process is profitable or not depends on proper growth. Therefore, numerous and rigorous measures are employed to maintain control over culture conditions. However, these cultures are prone to contamination by other microorganisms, or they can be infected by a great number of viruses, called bacteriophages or phages.

During phage infection, the phage recognize and attack their host cell in the lytic cycle until the host is completely destroyed releasing hundreds of viral particles which has the potential of attacking the remaining sensitive cells in the culture. Prior to the present invention, the threat of phage infection was one of the most serious problems affecting bacterial cultures of biotechnological interest leading to significant losses in the production process. This has led to the need of finding methods that allow for the generation of enhanced strains which are resistant to infection by bacteriophages.

U.S. Pat. No. 5,240,841A describes a method to generate an *E. coli* strain resistant to bacteriophage QB. This method consists of isolating a specific region of the corresponding viral replicase gene. This region encodes for the peptide moiety of the viral replicase, which has the function of binding the viral genome in a specific sequence for its replication. After being isolated, this moiety can be introduced in the *E. coli* genome. When expressed as a peptide, it competes for the binding site with viral replicase preventing the replication and spreading of the virus, which provides resistance to the host. However, in order to apply this strategy to all bacteriophages which infect *E. coli*, a peptide must be generated for each phage in an *E. coli* strain, which is inviable.

Hong J et al. (Hong, J. et al. Identification of host receptor and receptor-binding module of a newly sequenced T5-like phage EPS7. FEMS Microbiology letters. Vol 289(2). pp 202-209. 2008.) demonstrated that the BtuB protein, which is a transmembrane transporter in *E. coli* involved in the transport of vitamin B12, acts as a receptor of T5-like phage EPS7. By making a series of mutations of the encoding gene of this protein, btuB, the infection by phages was blocked demonstrating that this receptor has an important role during the adsorption process of the phage.

Knirel, Y A. et al. (Knirel, Y A. et al. Variations in O-antigen biosynthesis and O-acetylation associated with altered phage sensitivity in *Escherichia coli* 4s. Journal of Bacteriology. Vol 197(5). pp 905-912. 2015) describes variations in the synthesis and structure of antigen O of *E. coli* strain 4s isolated from fecal matter from horse. These mutations induce resistance to bacteriophage G7C and further modify the interaction of *E. coli* 4s with other different bacteriophages leading to both resistance and sensitivity to the host cell.

WO1997020917A2 describes the use of a gene called AbiE, which encodes for a protein that interrupts the infection by phages. This gene resides in native form in the *Lactococcus lactis* strain. This gene was isolated and cloned in plasmid pSRQ800. The transformation of *Lactococcus lactis* or other microorganisms used in the dairy industry gives resistance to infection by phages 936, c2 and P335.

WO2001007566A2 describes a genetic system capable of imparting resistance to infection by phages, which consists of two plasmids, pCRB33 and pCRB63. After transformation in *Streptococus thermophilus* strain, this strain acquires resistance to infection by phages. Plasmids encode for elements of a type 1 methylation-restriction system called "s" subunits. Both plasmids have these incomplete genetic elements. Due to the great homology in the sequence of "s" subunits, they recombine inside the cell producing a third plasmid (pCRB96). This recombination produces a complete ORF for the "S" subunit imparting resistance to phages.

CA2311598A1 describes a method and elements necessary for imparting resistance to phages in *Lactococcus lactis* and other strains used in dairy industry. This patent describes the use of an Abi900 protein encoded by plasmid pSRQ900. By being transformed by this plasmid in the strain of interest, resistance to phages 936, c2 and P335 by the infection interruption mechanism is provided.

Denes et al. (Denes, T., et. al., Appl Environ Microbiol, 81 (13), pp 4295-4305 (2015)) isolated strains of *Listeria monocytogenes* resistant to phages LP-048 and LP-125. By sequencing, they found mutations in two key loci for the adsorption of phages LP-048 and LP-125.

Proper phage isolation is necessary to corroborate that one has phage-resistant strains. Examples of phage-isolation protocols known in the art include: (1) (Uc-Mass, Augusto. et al. An orthologue of the cor gene is involved in the exclusion of temperature lambdoid phages. Evidence that Cor inactivates FhuA receptor functions. Virology., Vol 329. pp 425-433. 2004.) and (2) (Kameyama, Luis. et al. Characterization of wild lambdoid bacteriophages: detection of a wide distribution of phageimmunity groups and identification of a nus-dependent, nonlambdoid phage group. Virology. Vol 263. pp 100-111. 1999), or they can be acquired from microbial collections, such as the ATCC, etc.

It is important to note that prior to the present invention no disclosure has been made that relates mutations or deletions in tfaD and yejO genes to impart resistance to different types of phages which infect *E. coli.*

BRIEF SUMMARY OF THE INVENTION

The present invention provides a method for generating genetically modified microorganisms that are resistant to infection by different phages.

The present invention also provides genetically modified microorganisms that are resistant to infection by different phage families.

Further, the present invention provides *E. coli* strains that have point mutations or deletions in different genes, and which also impart resistance to various phage families.

The present invention provides *E. coli* strains that are resistant to phages of the Siphoviridae and Myoviridae families.

The present invention provides *E. coli* strains that are resistant to phages λ, ϕ80 and T4. Moreover, the present invention provides *E. coli* strains that are resistant to phages λ, Φ80 and T4 and that retain their kinetic constants relative to wild type strains.

The above objects highlight certain aspects of the invention. Additional objects, aspects and embodiments of the invention are found in the following detailed description of the invention.

BRIEF DESCRIPTION OF THE DRAWINGS

A more complete appreciation of the invention and many of the attendant advantages thereof will be readily obtained as the same becomes better understood by reference to the following Figures in conjunction with the detailed description below.

FIG. 3 shows a protein alignment of the wildtype TfaD protein (SEQ ID NO: 2) and the mutated TfaD protein (SEQ ID NO: 4).

FIG. 4 shows a protein alignment of the wildtype TfaD gene (SEQ ID NO: 1) and the mutated TfaD gene (SEQ ID NO: 3).

FIGS. 5A-5C show a protein alignment of the wildtype YejO protein (SEQ ID NO: 6) and the mutated YejO protein (SEQ ID NO: 8).

FIGS. 6A-6G show a protein alignment of the wildtype YejO gene (SEQ ID NO: 5) and the mutated YejO gene (SEQ ID NO: 7).

DETAILED DESCRIPTION OF THE INVENTION

Figure 1:
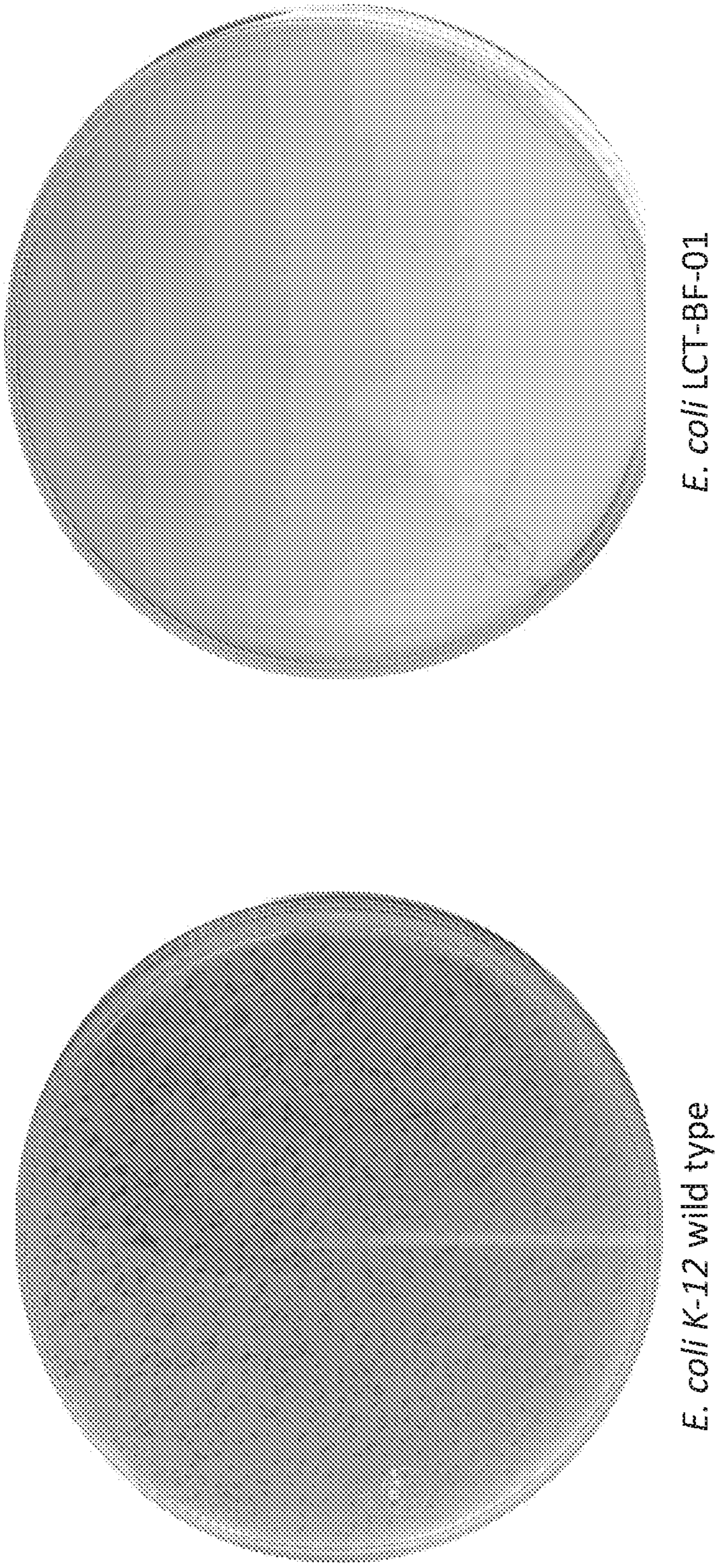
FIG. 1 shows the difference between wildtype *E. coli* K-12 and *E. coli* LCT-BF-01 strains infected by phage λ, Φ80 and T4 in M9 agar medium. It was observed that strain LCT-BF-01 grew normally, while the wild type strain exhibited lytic plaques which are indicative of cellular lysis.

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In order to better understand the object of the present invention, the following definitions and abbreviations are established.

The terms "gene" or "genes" refer to biological molecules composed of nitrogen compounds or nitrogen bases known in the state of the art, such as Adenine, Guanine, Cytosine and Thymine. Genes are molecules which transmit information in a cell for the biological synthesis of enzymes.

The term "locus" refers to the fixed position of a gene on a chromosome.

The term "loci" refers to the plural of "locus", i.e., the fixed positions of two or more genes on a chromosome.

The term "substrate" refers to a molecule which can be used as a carbon source for the microorganism to grow or to be used as a desired product. Examples of substrate can be carbohydrates, lipids, proteins, organic acids, alcohols, aldehydes, ketones, hydrocarbons, etc.

The term "deletion or removal of genes" refers to the procedure of totally or partially removing a gene, modifying the reading frame or adding a stop codon in any region of the gene other than the natural stop codon; it also refers to adding or removing regions which prevent the transcription and/or reduction of the gene.

The term "plaque-forming units" refers to cells which were infected by the bacteriophage or to the number of bacteriophages which infected a cell from the culture.

The terms "phages" or "bacteriophage" refer to a virus which is capable of infecting bacteria and which can produce the cell rupture of bacteria during the infection cycle. Examples of these phages can be M13, T4, Lambda or any other virus which is described in the state of the art which causes infection of bacteria, whether by the lytic cycle or lysogenic cycle. The lytic and lysogenic cycles of a phage are widely known by any person related to the field of the invention.

The term "biomass" refers to the total amount of organic matter which makes up the culture and which corresponds to a single type of microorganism, in this case, the producing strain and its exponential growth resulting from the fermentation process. Biomass is spectrophotometrically determined by optical density at 600 nm and by dry weight in thermoscale expressed in g/L.

The term "inoculum" refers to the initial biomass portion corresponding to the strain of interest to initiate the fermentation process.

The term "fermentation" refers to the catabolic metabolism in which the oxidation of the carbon source can be complete by having Oxygen as final electron acceptor or incomplete, wherein an organic compound is produced which functions as electron donor and electron acceptor at the same time and wherein ATP is produced by phosphorylation at substrate level.

The term "culture medium" refers to the solution which contains the necessary nutrients to allow the growth of the strain of interest. Known media in the state of the art are M9, LB 2YT, and any other medium which is reported in the state of the art which could be useful for the growth of the strain of interest.

The term "anaerobic conditions" refers to a fermentation period in which oxygen is fed to the reactor tank, which acts as ultimate electron acceptor and the oxidation of the carbon source is complete.

The term "expressed" refers to the gene or set of genes which are transcribed in certain conditions during fermentation.

The term "wild type strain" refers to an organism which retains the original genetic material of its species, i.e., its genetic information has not been modified.

The term "μ" refers to the specific rate of growth of the strain of interest, expressed in $h^{-1}$, which depends on the concentration of nutrients in the medium and on operating parameters, such as agitation and aeration.

The term "Qs" refers to the consumption of a specific substrate, expressed in (g/g*h), i.e., the mass of substrate consumed by biomass unit during a certain period.

The term "attenuated phage or bacteriophage" refers to a virus whose genome is capable of replicating together with that of its host and does not cause cellular death in a state called lysogeny.

The term "reactor" refers to a physical space built from a suitable material in which, in a controlled way, a chemical, biochemical or biological reaction can take place, or combinations thereof. Different types of reactors can be found in the state of the art. By way of example, reactors such as a continuous stirred-tank reactors (CSTR), piston flow reactors, fluidized bed reactors and packed bed reactors (PBR) are described. Some of the features of reactors are: a) their resistance to corrosion due to the reaction which is taking place; b) their capacity for monitoring and controlling operation variables, such as temperature, agitation, pH, concentration of dissolved gases, pressure, etc.; c) the operation mode, which can be continuous, semi-continuous or batch (different operation modes in which a reactor can work are described in the state of the art); d) the capacity of using different types of catalysts which will carry out the reaction, for example, the catalysts can be dissolved or trapped or immobilized (different modes in which a catalyst can carry out the reaction inside a reactor are described in the state of the art). The present invention provides a method that allows microorganisms sensitive to infection by phages to acquire resistance to infection by phages, due to genetic changes.

More specifically, the present invention provides a method that allows microorganisms sensitive to infection by phages to be resistant to infection by one or more phages at the same time.

Further, the present invention provides a method that allows microorganisms sensitive to infection by phages to be resistant to infection by one or more phages from the same family at the same time.

Further, the present invention provides a method that allows microorganisms sensitive to infection by phages to be resistant to infection by one or more phages from different families at the same time.

Moreover, the present invention provides microorganisms that are capable of resisting an infection by one or more types of phages due to mutations in certain genes.

Further, the present invention provides microorganisms that are capable of resisting an infection by one or more phage families due to genetic changes.

Finally, the present invention provides microorganisms that are capable of resisting an infection by one or more phage families and also retain the same kinetic constants.

In another embodiment of the present invention, a method for generating microorganisms resistant to infection by phage λ is provided, wherein the phage λ come into contact with the microorganism during a certain time to allow the infection. Subsequently, the culture is allowed to recover during a certain time. Bacteria which could survive the infection are isolated and biochemically, microbiologically and genetically characterized as follows:

I. In a flask containing M9 culture medium, the microorganism is allowed to grow until reaching an optical density from 0.6 to 5, more specifically from 1 to 3 and more specifically from 2 to 2.5.

II. Phage λ is added to the culture medium, wherein the concentration of the phage is at least 100 plaque-forming units, more specifically at least 250 plaque-forming units, and more specifically at least 500 plaque-forming units.

III. Phage infection is allowed from 30 minutes to 6 hours, more specifically from 2 hours to 4 hours, and more specifically from 2.5 hours to 3.5 hours at room temperature, more preferably at a temperature ranging from 20 to 25° C.

IV. The culture is allowed to lyse from 1 hour to 8 hours, more specifically from 3 hours to 6 hours and more specifically from 4 hours to 5 hours at 37° C., more preferably at a temperature ranging from 35 to 39° C.

V. The culture is allowed to recover from 1 hour to 24 hours, more specifically from 6 hours to 20 hours and more specifically from 10 hours to 16 hours. Recovery may be at room temperature, more preferably at a temperature ranging from 20 to 25° C.

VI. Colonies are isolated into plates with M9 medium or with other medium suitable for cell growth.

VII. It is verified that the colonies are resistant to phage 2 by repeating steps I to VI at least twice.

In another embodiment of the present invention, a method for generating microorganisms resistant to infection by phage $80 is provided, wherein the phage $80 come into contact with the microorganism during a certain time to allow the infection. Subsequently, the culture is allowed to recover during a certain time. Bacteria which could survive the infection are isolated and biochemically, microbiologically and genetically characterized as follows:

I. In a flask containing M9 culture medium, the microorganism is allowed to grow until reaching an optical density from 0.6 to 5, more specifically from 1 to 3 and more specifically from 2 to 2.5

II. Phage Φ80 is added to the culture medium, wherein the concentration of the phage is at least 100 plaque-forming units, more specifically at least 250 plaque-forming units, and more specifically at least 500 plaque-forming units.

III. Phage infection is allowed from 30 minutes to 6 hours, more specifically from 2 hours to 4 hours, and more specifically from 2.5 hours to 3.5 hours at room temperature, more preferably at a temperature ranging from 20 to 25° C.

IV. The culture is allowed to lyse from 1 hour to 8 hours, more specifically from 3 hours to 6 hours and more specifically from 4 hours to 5 hours at 37° C., more preferably at a temperature ranging from 35 to 39° C.

V. The culture is allowed to recover from 1 hour to 24 hours, more specifically from 6 hours to 20 hours and more specifically from 10 hours to 16 hours. Recovery may be at room temperature, more preferably at a temperature ranging from 20 to 25° C.

VI. Colonies are isolated into plates with M9 medium or with other medium suitable for cell growth.

VII. It is verified that the colonies are resistant to phage Φ80 by repeating steps I to VI at least twice.

In another embodiment of the present invention, a method for generating microorganisms resistant to infection by phage T4 is provided, wherein the phage T4 come into contact with the microorganism during a certain time to allow the infection. Subsequently, the culture is allowed to recover during a certain time. Bacteria which could survive the infection are isolated and biochemically, microbiologically and genetically characterized as follows:

I. In a flask containing M9 culture medium, the microorganism is allowed to grow until reaching an optical density from 0.6 to 5, more specifically from 1 to 3 and more specifically from 2 to 2.5.

II. Phage T4 is added to the culture medium, wherein the concentration of the phage is at least 100 plaque-forming units, more specifically at least 250 plaque-forming units, and more specifically at least 500 plaque-forming units.

III. Phage infection is allowed from 30 minutes to 6 hours, more specifically from 2 hours to 4 hours, and more specifically from 2.5 hours to 3.5 hours at room temperature, more preferably at a temperature ranging from 20 to 25° C.

IV. The culture is allowed to lyse from 1 hour to 8 hours, more specifically from 3 hours to 6 hours and more specifically from 4 hours to 5 hours at 37° C., more preferably at a temperature ranging from 35 to 39° C.

V. The culture is allowed to recover from 1 hour to 24 hours, more specifically from 6 hours to 20 hours and more specifically from 10 hours to 16 hours. Recovery may be at room temperature, more preferably at a temperature ranging from 20 to 25° C.

VI. Colonies are isolated into plates with M9 medium or with other medium suitable for cell growth.

VII. It is verified that the colonies are resistant to phage T4 by repeating steps I to VI at least twice.

In another embodiment of the present invention, a method for generating bacteria from the *E. coli* genus which have mutations in the tfaD and yejO genes and which are also resistant to infection by phages is provided, wherein the phages come into contact with the microorganism during a certain time to allow the infection. Subsequently, the culture is allowed to recover during a certain time. Bacteria which could survive the infection are isolated and biochemically, microbiologically and genetically characterized as follows:

I. To an *E. coli* strain, mutations are made in the tfaD and yejO genes.

II. In a flask containing M9 culture medium, the *E. coli* strain is allowed to grow with the tfaD and yejO mutations until reaching an optical density from 0.6 to 5, more specifically 1 to 3 and more specifically 2 to 2.5.

III. Phages λ, Φ80 and T4 and are added to the culture medium, separately or mixed, wherein the concentration of the phage is at least 100 plaque-forming units, more specifically at least 250 plaque-forming units, and more specifically at least 500 plaque-forming units.

IV. Phage infection is allowed from 30 minutes to 6 hours, more specifically from 2 hours to 4 hours, and more specifically from 2.5 hours to 3.5 hours at room temperature, more preferably at a temperature ranging from 20 to 25° C.

V. The culture is allowed to lyse from 1 hour to 8 hours, more specifically from 3 hours to 6 hours and more specifically from 4 hours to 5 hours at 37° C., more preferably at a temperature ranging from 35 to 39° C.

VI. The culture is allowed to recover from 1 hour to 24 hours, more specifically from 6 hours to 20 hours and more specifically from 10 hours to 16 hours. Recovery may be at room temperature, more preferably at a temperature ranging from 20 to 25° C.

VII. Colonies are isolated into plates with M9 medium or with other medium suitable for cell growth.

VIII. It is verified that the colonies are resistant to the phages λ, Φ80 and T4, separately or mixed by repeating steps I to VII at least twice.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

EXAMPLES

The following examples are intended to clarify the novelty of the present invention. It should be understood that the following examples do not limit the scope of the present invention. From the disclosure of the invention, as well as the following examples, a person skilled in the field of the invention can make some modifications, which in any way remain within the framework protected by this invention.

Example 1. Generation of Strains Resistant to Phages λ, Φ80 and T4

In the case of the present invention, different environment phages which infect different microorganisms were isolated, although, to exemplify the method of the present invention, the *E. coli* bacteria was used.

Different culture media were used to make bacteria come into contact with phages. Some of the media were LB agar medium and M9 agar medium (Sambrook, J., and Green, M. (2012). Molecular cloning: a laboratory manual, 4th edition. Cold Spring Harbor Laboratory, Cold Spring Harbor, New York).

A culture of wild type *E. coli* K-12 in liquid M9 medium was prepared, it was left to grow from 6 hours to 24 hours, after that, a mixture of phages λ, Φ80 and T4 was added. A cycle of infection was allowed from 30 minutes to 6 hours at room temperature. Thereafter, the culture was incubated at 30° C. from 1 hour to 8 hours for the culture to clarify, in this moment most of the cells are dead. Subsequently, incubation was continued to allow for the reproduction of phage-resistant cells. After a period from 1 hour to 24 hours, it was observed that the culture starts growing again and it was taken as inoculum to isolate the resistant colonies.

Plates were seeded by extension in M9 agar. After 16 hours of incubation at 37° C., phage-resistant colonies were observed and were selected to be infected again.

Selected candidate colonies were challenged against the phage by the pour plate method. First, a culture was left to grow in liquid from the strain of interest for 6 hours, subsequently, it was infected with the phage allowing for an infection cycle to happen for 1 hour at room temperature. Thereafter, infected cells were mixed in soft M9 agar medium and were incubated for 16 h at 37° C. At the end of this incubation period, it was observed that resistant strains did not exhibit lytic plaques, while sensitive strains did (FIG. 1).

Isolated colonies were subjected to at least 5 infection and isolation cycles. After the infection and isolation cycles, strains were biochemically, microbiologically and genetically reviewed in order to verify that genetic modifications made at the beginning were the cause of the resistance. The strain that resisted infection by the tested phages was named LCT-BF-01.

In order to demonstrate that strain LCT-BF-01 was resistant to phages λ, Φ80 and T4 and grew in liquid medium, cultures in a 14 L reactor were made using M9 medium at different operating conditions. The operating conditions are shown in Table 1.

TABLE 1

Operating conditions of the reactor.

| Condition | Values |
|---|---|
| pH | 6.8-8 |
| Temperature | 20-40° C. |
| Dissolved oxygen | 0.1-8 mg/L |

Figure 2:
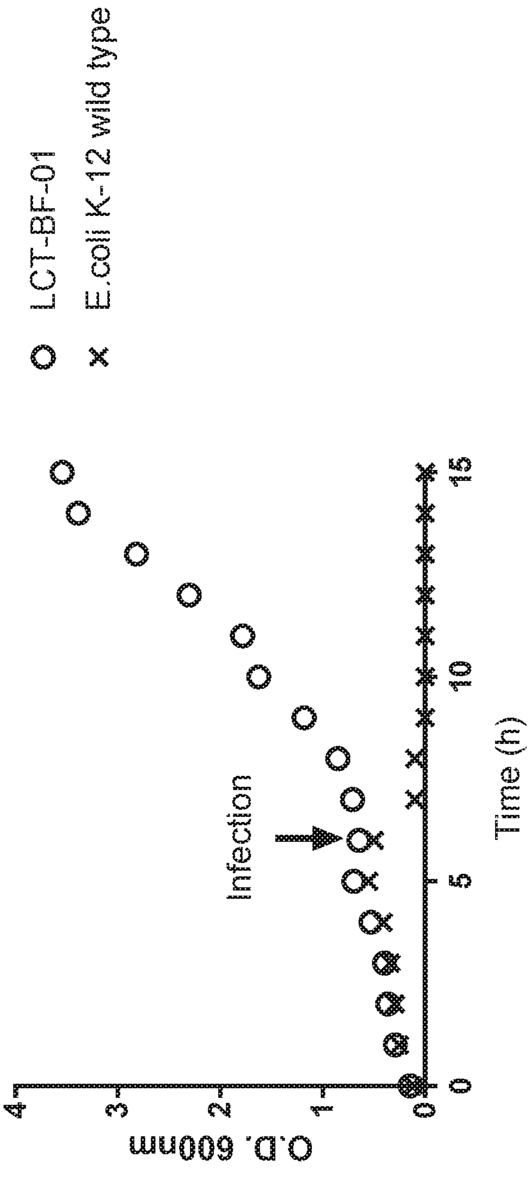
FIG. 2 shows the difference between growth of *E. coli* LCT-BF-01 and wild type *E. coli* K-12 strains in liquid M9 medium before and after infection by phages λ, Φ80 and T4. LCT-BF-01 strain is resistant to infection by bacteriophages, while wild type K12 strain is lysed. Growth kinetics of wild type strains (X) and LCT-BF-01 strain (O). The arrow indicates the point where cultures are infected with the phage mixture.

The reactor was prepared, sterilized at 121° C. and pressure of 15 psig, inoculated with a colony from strain LCT-BF-01 with sterilization and was allowed to grow for six hours. Subsequently, it was infected by a mixture of phages λ, Φ80 and T4 and its growth, pH, temperature and oxygen were further monitored in the reactor. After 16 hours of growth, it was observed that the culture did not clarify in any moment during fermentation (FIG. 2). The same experiment was made with the wild type *E. coli* K-12 strain, this strain did not exhibit growth after infection (FIG. 2). With this example it was demonstrated that strain LCT-BF-01 is resistant to phages λ, Φ80 and T4.

Subsequently, strain LCT-BF-01 was sequenced in an Illumina MiniSeq System sequencer, using the bacterial sequencing kit and following the manufacturer's instructions (Illumina Inc.), in order to corroborate the generated mutations. In table 2, genes that underwent mutations during the corresponding infection process are shown.

TABLE 2

Identified mutations in different *E. coli* genes

| Gene | Position of mutation in protein | Aminoacid changed |
|---|---|---|
| TfaD | 69 | A->T |
| YejO | 23 | W->R |

TfaD wildtype gene appears as SEQ ID NO: 1 and the wildtype TfaD protein appears as SEQ ID NO: 2. The mutated TfaD gene appears as SEQ ID NO: 3 and the corresponding mutated TfaD protein appears as SEQ ID NO: 4.

YejO wildtype gene appears as SEQ ID NO: 5 and the wildtype YejO protein appears as SEQ ID NO: 6. The mutated YejO gene appears as SEQ ID NO: 7 and the corresponding mutated YejO protein appears as SEQ ID NO: 8.

Example 2. Comparison of Kinetic Parameters of Strains LCT-BF-01 and Wild Type *E. Coli* K-12 Strain Strains LCT-BF-01 and wild type *E. coli* K-12 were cultured in M9 medium in a 14 L reactor in order to determinate the kinetic parameters in aerobic conditions. The culture took 24 h, the operating conditions are shown in Table 3.

TABLE 3

Operating conditions of the reactor.

| Condition | Values |
|---|---|
| pH | 7 |
| Temperature | 37° C. |
| Dissolved oxygen | 2 mg/L |

The concentration of glucose and organic acids were monitored during fermentation using an HPLC Ultimate 3000 equipment (Thermo) with an index of refraction detector using a Rezex-ROA organic acids $H^+$ column. Results of fermentations are shown in Table 4.

TABLE 4

Kinetic constants of strains LCT-BF-01 and Wild type

| Variable | Strain LCT-BF-01 | Wild type (WT) |
|---|---|---|
| μ | 0.44 | 0.45 |
| Qs | 0.88 | 0.89 |

These results demonstrate that strains developed in the present invention are resistant to phages from different families and have the same kinetic constants as WT, in spite of having mutations of TfaD and YejO genes.

Numerous modifications and variations on the present invention are possible in light of the above teachings. It is, therefore, to be understood that within the scope of the accompanying claims, the invention may be practiced otherwise than as specifically described herein.

REFERENCES

Denes, T., et. al., 2015. Appl Envirom Microbiol, 81 (13), pp 4295-4305.

Hong, J. et al. Identification of host receptor and receptor-binding module of a newly sequenced T5-like phage EPS7. FEMS Microbiology letters. Vol 289(2). pp 202-209. 2008.

Kameyama, Luis. et al. Characterization of wild lambdoid bacteriophages: detection of a wide distribution of phageimmunity groups and identification of a nus-dependent, nonlambdoid phage group. Virology. Vol 263. pp 100-111. 1999.

Knirel, Y A. et al. Variations in O-antigen biosynthesis and O-acetylation associated with altered phage sensitivity in *Escherichia coli* 4s. Journal of Bacteriology. Vol 197(5). pp 905-912. 2015.

Sambrook, J., and Green, M. (2012). Molecular cloning: a laboratory manual, 4th edition. Cold Spring Harbor Laboratory, Cold Spring Harbor, New York.

Uc-Mass, Augusto. et al. An orthologue of the cor gene is involved in the exclusión of temperatura lambdoid phages. Evidence that Cor inactivates FhuA receptor functions. Virology., Vol 329. pp 425-433. 2004.

Wang, X., Kim, Y., Ma, Q., Hong, S. H., Pokusaeva, K., Sturino, J. M., & Wood, T. K. (2010). Cryptic prophages help bacteria cope with adverse environments. Nature communications, 1, 147).

Patent: CA2311598A1

Patent: EP2534252B1

Patent: WO1997020917A2

Patent: WO2001007566A2

Having described the invention, the contents of the following claims is claimed as property:

1. A method for generating genetically modified microorganisms from *Escherichia coli* (*E. coli*) strains resistant to infection by phages, the method comprising:

a) making mutations in tfaD and yejO genes of an *E. coli* strain that is sensitive to infection by phages;

b) growing the *E. coli* strain having mutations in the tfaD and yejO genes in a culture medium, thereby forming a culture of the *E. coli* strain, until the *E. coli* strain reaches an optical density at 600 nm from 2 to 5;

c) adding phages λ, ϕ80 and T4 to the culture medium, the phages having a concentration greater than 100 plaque-forming units;

d) contacting the culture of the *E. coli* strain with the phages for 30 minutes to 6 hours at a temperature of 20° C. to 25° C. to allow for infection by the phages;

e) allowing for cellular lysis for 1 hour to 8 hours at a temperature of 35° C. to 39° C.;

f) allowing the culture of the *E. coli* strain to recover for 1 hour to 24 hours;

g) isolating colonies into plates with culture medium; and h) verifying the resistance to infection by phages λ, ϕ80 and T4 of the *E. coli* strain generated by steps a) to g) by repeating steps a) to g);

wherein the adding comprises separately adding the phages λ, ϕ80 and T4 to the culture medium to form a mixture of phages or adding a mixture containing the phages 2, $80 and T4 to the culture medium, wherein a genetically modified microorganism is generated from the *E. coli* strain resistant to infection by phages λ, Φ80 and T4, the method further comprising verifying the resistance to infection by phages λ, ϕ80 and T4 of the *E. coli* strain was caused by mutations in the tfaD and yejO genes of said *E. coli* strain by:

growing the *E. coli* strain having mutations in the tfaD and yejO genes in the culture medium in a reactor at different operating conditions of the reactor, the different operating conditions of the reactor comprise one or more of pH, temperature, and/or dissolved oxygen;

determining the culture of the *E. coli* strain did not clarify during fermentation; and sequencing the *E. coli* strain to corroborate that the mutations in the tfaD and yejO genes of the *E. coli* strain were the cause of the resistance to infection by the phages λ, ϕ80 and T4, the method also further comprising identifying that mutation in the tfaD gene of the *E. coli* strain corresponds to a mutated TfaD protein, the mutated TfaD protein containing a mutation at position 69 of said TfaD protein; and identifying that mutation in the yejO gene of the *E. coli* strain corresponds to a mutated YejO protein, the mutated YejO protein containing a mutation at position 23 of said YejO protein.

2. The method according to claim 1, comprising:

repeating steps a) to g) at least twice.

3. The method according to claim 1, comprising:

acquiring, by the *E. coli* which is sensitive to infection by phages and which is a wild type strain, resistance to infection by phages while retaining at least the same kinetic constants μ and Qs as the wild type strain.

4. The method according to claim 1, wherein the contacting comprises contacting the *E. coli* culture with phages for 2 hours to 4 hours.

5. The method according to claim 1, wherein the allowing of e) or f) comprises one or more of:

allowing the *E. coli* culture to recover at a temperature of 20° C. to 25° C.; and/or allowing for cellular lysis for 3 hours to 6 hours.

* * * * *

SEQUENCE LISTING

<160> NUMBER OF SEQ ID NOS: 8

<210> SEQ ID NO 1
<211> LENGTH: 438
<212> TYPE: DNA
<213> ORGANISM: Artificial Sequence
<220> FEATURE:
<223> OTHER INFORMATION: Synthetic tfaD wildtype gene

<400> SEQUENCE: 1

```
attccagctg gcttcgtggc tgttttcaac agtgatgagt catcgtggca tctcgttgaa     60

gatcatcggg gtaaaacggt ttatgacgta gcgtcagggg acgcgttatt tatttctgaa    120

ctcggtccgt taccggaaaa tgttacctgg ttatcgccgg aaggggagtt tcagaagtgg    180

aacggtacag cctgggtgaa agatgcagaa gcagaaaaac tgttccggat tcgggaggcg    240

gaagaaacaa aaaacagcct gatgcaggta gccagtgagc atattgcgcc acttcaggat    300

gctgtagatc tggaaatcgc aacggaggaa gaaacctcat tgctggaagc ctggaaaaaa    360

tatcgggtgt tgctgaaccg tgttgataca tcaactgcac ctgatattga gtggcctacg    420

aaccctgtca gggagtaa                                                  438
```

<210> SEQ ID NO 2
<211> LENGTH: 145
<212> TYPE: PRT
<213> ORGANISM: Artificial Sequence
<220> FEATURE:
<223> OTHER INFORMATION: Synthetic tfaD wildtype protein

<400> SEQUENCE: 2

```
Ile Pro Ala Gly Phe Val Ala Val Phe Asn Ser Asp Glu Ser Ser Trp
1               5                   10                  15

His Leu Val Glu Asp His Arg Gly Lys Thr Val Tyr Asp Val Ala Ser
            20                  25                  30

Gly Asp Ala Leu Phe Ile Ser Glu Leu Gly Pro Leu Pro Glu Asn Val
        35                  40                  45

Thr Trp Leu Ser Pro Glu Gly Glu Phe Gln Lys Trp Asn Gly Thr Ala
    50                  55                  60

Trp Val Lys Asp Ala Glu Ala Glu Lys Leu Phe Arg Ile Arg Glu Ala
65                  70                  75                  80

Glu Glu Thr Lys Asn Ser Leu Met Gln Val Ala Ser Glu His Ile Ala
                85                  90                  95

Pro Leu Gln Asp Ala Val Asp Leu Glu Ile Ala Thr Glu Glu Glu Thr
            100                 105                 110

Ser Leu Leu Glu Ala Trp Lys Lys Tyr Arg Val Leu Leu Asn Arg Val
        115                 120                 125

Asp Thr Ser Thr Ala Pro Asp Ile Glu Trp Pro Thr Asn Pro Val Arg
    130                 135                 140

Glu
145
```

<210> SEQ ID NO 3
<211> LENGTH: 400
<212> TYPE: DNA
<213> ORGANISM: Artificial Sequence
<220> FEATURE:
<223> OTHER INFORMATION: Synthetic tfaD mutated gene

<400> SEQUENCE: 3

```
attccagctg gcttcgtggc tgttttcaac agtgatgagt catcgtggca tctcgttgaa     60
```

-continued

```
gatcatcggg gtaaaacggt ttatgacgtg gcttccggcg acgcgttatt tatttctgaa    120

ctcggtccgt taccggaaaa tgttacctgg ttatcgccgg aaggggagtt tcagaagtgg    180

aacggcacag cctgggtgaa ggatacggaa gcagaaaaac tgttccggat ccgggaggcg    240

gaagaaacaa aaaacagcct gatgcaggta gccagtgagc atattgcgcc acttcaggat    300

gctgtagatc tggaaatcgc aacggaggaa gaaacctcat tgctggaagc ctggaaaaaa    360

tatcgggtgt tgctgaaccg tgttgataca tcaactgcac                          400
```

<210> SEQ ID NO 4
<211> LENGTH: 145
<212> TYPE: PRT
<213> ORGANISM: Artificial Sequence
<220> FEATURE:
<223> OTHER INFORMATION: Synthetic tfaD mutated protein

<400> SEQUENCE: 4

```
Ile Pro Ala Gly Phe Val Ala Val Phe Asn Ser Asp Glu Ser Ser Trp
1               5                   10                  15

His Leu Val Glu Asp His Arg Gly Lys Thr Val Tyr Asp Val Ala Ser
            20                  25                  30

Gly Asp Ala Leu Phe Ile Ser Glu Leu Gly Pro Leu Pro Glu Asn Val
        35                  40                  45

Thr Trp Leu Ser Pro Glu Gly Glu Phe Gln Lys Trp Asn Gly Thr Ala
    50                  55                  60

Trp Val Lys Asp Thr Glu Ala Glu Lys Leu Phe Arg Ile Arg Glu Ala
65                  70                  75                  80

Glu Glu Thr Lys Asn Ser Leu Met Gln Val Ala Ser Glu His Ile Ala
                85                  90                  95

Pro Leu Gln Asp Ala Val Asp Leu Glu Ile Ala Thr Glu Glu Glu Thr
            100                 105                 110

Ser Leu Leu Glu Ala Trp Lys Lys Tyr Arg Val Leu Leu Asn Arg Val
        115                 120                 125

Asp Thr Ser Thr Ala Pro Asp Ile Glu Trp Pro Thr Asn Pro Val Arg
    130                 135                 140

Glu
145
```

<210> SEQ ID NO 5
<211> LENGTH: 3791
<212> TYPE: DNA
<213> ORGANISM: Artificial Sequence
<220> FEATURE:
<223> OTHER INFORMATION: Synthetic yejO wildtype gene

<400> SEQUENCE: 5

```
atgcatcaat ctggttctgt ttctctttgt cgttccgcaa tatctgttct ggtggctaca     60

gcgttatgga aggtgcgaac aagtccctga tatgagatca tgtttgtcat ctggagccat    120

agaacagggt tcatcatgag tcatcaactt accttcgccg acagtgaatt cagcagtaag    180

cgccgtcaga ccagaaaaga gattttcttg tcccgcatgg agcagattct gccatggcaa    240

aacatggtgg aagtcatcga gccgttttac cccaaggctg gtaatggccg gcgaccttat    300

ccgctggaaa ccatgctacg cattcactgc atgcagcatt ggtacaacct gagcgatggc    360

gcgatggaag atgctctgta cgaaatcgcc tccatgcgtc tgtttgcccg gttatccctg    420

gatagcgcct tgccggaccg caccaccatc atgaatttcc gccacctgct ggagcagcat    480
```

-continued

```
caactggccc gccaattgtt caagaccatc aatcgctggc tggccgaagc aggcgtcatg    540

atgactcaag gcaccttggt cgatgccacc atcattgagg cacccagctc gaccaagaac    600

aaagagcagc aacgcgatcc ggagatgcat cagaccaaga aaggcaatca gtggcacttt    660

ggcatgaagg cccacattgg tgtcgatgcc aagagtggcc tgacccacag cctggtcacc    720

accgcggcca acgagcatga cctcaatcag ctgggtaatc tgctgcatgg agaggagcaa    780

tttgtctcag ccgatgccgg ctaccaaggg gcgccacagc gcgaggagct ggccgaggtg    840

gatgtggact ggctgatcgc cgagcgcccc ggcaaggtaa gaaccttgaa acagcatcca    900

cgcaagaaca aaacggccat caacatcgaa tacatgaaag ccagcatccg ggccagggtg    960

gagcacccat ttcgcatcat caagcgacag ttcggcttcg tgaaagccag atacaagggg   1020

ttgctgaaaa acgataacca actggcgatg ttattcacgc tggccaacct gtttcgggcg   1080

gaccaaatga tacgtcagtg ggagagatct cactaaaaac tggggataac gccttaaatg   1140

gcgaagaaac ggtctaaata ggctgattca aggcatttac gggagaaaaa atcggctcaa   1200

acatgaagaa atgaaatgac tgagtcagcc gagaagaatt tccccgctta ttcgcacctt   1260

ccttatattc acccatagca ttggcatcaa ctgttgagta tggtgagaca gttgatggtg   1320

ttgtcctgga aaaagatatc cagctggttt atgggaccgc caataatacg aaaatcaatc   1380

ctggcggaga acagcatata aaagaatttg gtgtaagtaa taatactgaa attaacggag   1440

ggtatcagta cattgaaatg aatggcgccg cagaatactc agtattaaat gacggttatc   1500

aaattgttca aatgggtggc gcggcaaacc agactacgct caataatggt gtgctacagg   1560

tttatggcgc agcgaatgat accacgatta aaggcgggcg cttaatcgtt gaaaaagatg   1620

ggggggccgt ctttgtcgct atcgaaaagg gaggactact ggaggttaaa gaggggggat   1680

ttgcatttgc ggtagatcag aaagcaggcg gtgctattaa aacaaccacg cgggccatgg   1740

aggtattcgg aacaaaccgt ctcggtcagt tcgatatcaa gaatggtatt gctaataata   1800

tgttgttgga aaacggcgga agtttgcgag ttgaagaaaa tgacttcgct tataatacca   1860

ctgtagatag tggcggctta ctggaggtta tggatggcgg gactgtaact ggcgttgata   1920

aaaaagcagg cggaaaatta attgtctcaa cgaatgcgct ggaagtgagt ggtccaaaca   1980

gtaaaggcca atttagtata aaagatggtg tgtcaaaaaa ttatgaactg gatgatggtt   2040

ccgggctcat tgttatggag gacacgcagg ccattgatac tatccttgat aagcatgcca   2100

ctatgcaatc gctgggaaag gatactggta cgaaagtgca ggcaaatgcg gtatatgatc   2160

tcggtcgatc atatcagaat ggaagtatca cgtattcctc aaaagccatc tctgaaaata   2220

tggttatcaa caatggccgc gctaacgtct gggctggcac aatggttaac gtttcagtca   2280

gagggaatga tggcattctt gaggtcatga agccgcaaat aaattatgca cccgcaatgt   2340

tggtgggtaa ggtagtggtt tctgagggcg cttcttttag aacgcatggt gccgtggata   2400

ccagcaaagc ggacgtttcg ctcgaaaata gcgtatggac catcattgcc gatatcacta   2460

cgacgaacca aaacaccctc ctcaacttag ccaaccttgc gatgtctgac gcaaatgtga   2520

ttatgatgga tgagccagtg actcgttcat cagtgacggc aagtgcggaa aatttcatta   2580

cgttgaccac caataccctg tcgggaaacg gcaattttta tatgcgtacc gatatggcta   2640

atcatcagag cgatcagctc aacgtcaccg gtcaggcaac aggtgatttc aaaatattcg   2700

tgacggacac cggtgccagc ccggcagcag gagatagcct tacactggta acaacgggcg   2760

gcggtgatgc tgcatttacg ttgggcaatg ccggaggcgt tgttgatatc ggtacgtatg   2820

aatatacctt gctggataat ggcaaccata gctggagtct ggcagagaat cgcgcgcaaa   2880
```

```
ttaccccttc aaccactgat gtgctgaata tggcggccgc acaaccgctg gtatttgatg   2940

cagaactgga caccgtgcgt gagcgtcttg gtagcgtaaa aggcgttagt tacgatacgg   3000

cgatgtggag ttcggcaatt aacacccgca acaacgtgac cactgatgcg ggagctggtt   3060

ttgagcaaac attgacgggc ctgacgctcg gtatcgatag ccgtttctcc cgtgaagaaa   3120

gcagtacaat tcgcggcttg atctttggtt actctcattc tgatattggt tttgatcgcg   3180

gcggcaaagg taatatcgat agctataccc tgggggctta tgccggttgg gagcatcaga   3240

acggtgccta tgttgatggg gtggtgaaag ttgaccgttt tgccaacacc atccatggca   3300

agatgagtaa tggggcaaca gcgtttggcg attacaatag taacggcgcg ggtgctcatg   3360

ttgagagcgg gttccgttgg gttgacggat tgtggagtgt tagaccctat ctggccttta   3420

ccggctttac cacagatggt caggactaca cgttatcaaa cggcatgcgc gcggatgtgg   3480

gaaatacccg gatattacgc gctgaagcgg gaacggcggt aagctatcac atggacctgc   3540

aaaacggtac gacgctggaa ccctggctga aagcggccgt gcgtcaggaa tacgccgatt   3600

ctaaccaggt gaaagttaat gacgatggca aatttaataa tgatgtggct ggaaccagtg   3660

gcgtttatca ggctggtata aggtcatcgt ttaccccgac gttaagcggt catttgtcag   3720

tcagctatgg caatggcgca ggggtagaat cgccgtggaa tactcaggcg ggtgtggtct   3780

ggacgttctg a                                                        3791
```

<210> SEQ ID NO 6
<211> LENGTH: 1221
<212> TYPE: PRT
<213> ORGANISM: Artificial Sequence
<220> FEATURE:
<223> OTHER INFORMATION: Synthetic yejO wildtype protein

<400> SEQUENCE: 6

```
Met His Gln Ser Gly Ser Val Ser Leu Cys Arg Ser Ala Ile Ser Val
1               5                   10                  15

Leu Val Ala Thr Ala Leu Trp Lys Val Arg Thr Ser Pro Tyr Glu Ile
            20                  25                  30

Met Phe Val Ile Trp Ser His Arg Thr Gly Phe Ile Met Ser His Gln
        35                  40                  45

Leu Thr Phe Ala Asp Ser Glu Phe Ser Ser Lys Arg Arg Gln Thr Arg
    50                  55                  60

Lys Glu Ile Phe Leu Ser Arg Met Glu Gln Ile Leu Pro Trp Gln Asn
65                  70                  75                  80

Met Val Glu Val Ile Glu Pro Phe Tyr Pro Lys Ala Gly Asn Gly Arg
                85                  90                  95

Arg Pro Tyr Pro Leu Glu Thr Met Leu Arg Ile His Cys Met Gln His
            100                 105                 110

Trp Tyr Asn Leu Ser Asp Gly Ala Met Glu Asp Ala Leu Tyr Glu Ile
        115                 120                 125

Ala Ser Met Arg Leu Phe Ala Arg Leu Ser Leu Asp Ser Ala Leu Pro
    130                 135                 140

Asp Arg Thr Thr Ile Met Asn Phe Arg His Leu Leu Glu Gln His Gln
145                 150                 155                 160

Leu Ala Arg Gln Leu Phe Lys Thr Ile Asn Arg Trp Leu Ala Glu Ala
                165                 170                 175

Gly Val Met Met Thr Gln Gly Thr Leu Val Asp Ala Thr Ile Ile Glu
            180                 185                 190
```

-continued

```
Ala Pro Ser Ser Thr Lys Asn Lys Glu Gln Gln Arg Asp Pro Glu Met
        195                 200                 205

His Gln Thr Lys Lys Gly Asn Gln Trp His Phe Gly Met Lys Ala His
    210                 215                 220

Ile Gly Val Asp Ala Lys Ser Gly Leu Thr His Ser Leu Val Thr Thr
225                 230                 235                 240

Ala Ala Asn Glu His Asp Leu Asn Gln Leu Gly Asn Leu Leu His Gly
                245                 250                 255

Glu Glu Gln Phe Val Ser Ala Asp Ala Gly Tyr Gln Gly Ala Pro Gln
            260                 265                 270

Arg Glu Glu Leu Ala Glu Val Asp Val Asp Trp Leu Ile Ala Glu Arg
        275                 280                 285

Pro Gly Lys Val Arg Thr Leu Lys Gln His Pro Arg Lys Asn Lys Thr
    290                 295                 300

Ala Ile Asn Ile Glu Tyr Met Lys Ala Ser Ile Arg Ala Arg Val Glu
305                 310                 315                 320

His Pro Phe Arg Ile Ile Lys Arg Gln Phe Gly Phe Val Lys Ala Arg
                325                 330                 335

Tyr Lys Gly Leu Leu Lys Asn Asp Asn Gln Leu Ala Met Leu Phe Thr
            340                 345                 350

Leu Ala Asn Leu Phe Arg Ala Asp Gln Met Ile Arg Gln Trp Glu Arg
        355                 360                 365

Ser His Lys Leu Gly Ile Thr Pro Met Ala Lys Lys Arg Ser Lys Ala
    370                 375                 380

Asp Ser Arg His Leu Arg Glu Lys Lys Ser Ala Gln Thr Arg Asn Glu
385                 390                 395                 400

Met Thr Glu Ser Ala Glu Lys Asn Phe Pro Ala Tyr Ser His Leu Pro
                405                 410                 415

Tyr Ile His Pro His Trp His Gln Leu Leu Ser Met Val Arg Gln Leu
            420                 425                 430

Met Val Leu Ser Trp Lys Lys Ile Ser Ser Trp Phe Met Gly Pro Pro
        435                 440                 445

Ile Ile Arg Lys Ser Ile Leu Ala Glu Asn Ser Ile Lys Asn Leu Val
    450                 455                 460

Val Ile Ile Leu Lys Leu Thr Glu Gly Ile Ser Thr Leu Lys Met Ala
465                 470                 475                 480

Pro Gln Asn Thr Gln Tyr Met Thr Val Ile Lys Leu Phe Lys Trp Val
                485                 490                 495

Ala Arg Gln Thr Arg Leu Arg Ser Ile Met Val Cys Tyr Arg Phe Met
            500                 505                 510

Ala Gln Arg Met Ile Pro Arg Leu Lys Ala Gly Ala Ser Leu Lys Lys
        515                 520                 525

Met Gly Gly Pro Ser Leu Ser Leu Ser Lys Arg Glu Asp Tyr Trp Arg
    530                 535                 540

Leu Lys Arg Gly Asp Leu His Leu Arg Ile Arg Lys Gln Ala Val Leu
545                 550                 555                 560

Leu Lys Gln Pro Arg Gly Pro Trp Arg Tyr Ser Glu Gln Thr Val Ser
                565                 570                 575

Val Ser Ser Ile Ser Arg Met Val Leu Leu Ile Ile Cys Cys Trp Lys
            580                 585                 590

Thr Ala Glu Val Cys Glu Leu Lys Lys Met Thr Ser Leu Ile Ile Pro
        595                 600                 605

Leu Ile Val Ala Ala Tyr Trp Arg Leu Trp Met Ala Gly Leu Leu Ala
```

-continued

```
    610                 615                 620

Leu Ile Lys Lys Gln Ala Glu Asn Leu Ser Gln Arg Met Arg Trp Lys
625                 630                 635                 640

Val Val Gln Thr Val Lys Ala Asn Leu Val Lys Met Val Cys Gln Lys
                645                 650                 655

Ile Met Asn Trp Met Met Val Pro Gly Ser Leu Leu Trp Arg Thr Arg
            660                 665                 670

Arg Pro Leu Ile Leu Ser Leu Ile Ser Met Pro Leu Cys Asn Arg Trp
        675                 680                 685

Glu Arg Ile Leu Val Arg Lys Cys Arg Gln Met Arg Tyr Met Ile Ser
    690                 695                 700

Val Asp His Ile Arg Met Glu Val Ser Arg Ile Pro Gln Lys Pro Ser
705                 710                 715                 720

Leu Lys Ile Trp Leu Ser Thr Met Ala Ala Leu Thr Ser Gly Leu Ala
                725                 730                 735

Gln Trp Leu Thr Phe Gln Ser Glu Gly Met Met Ala Phe Leu Arg Ser
            740                 745                 750

Ser Arg Lys Ile Met His Pro Gln Cys Trp Trp Val Arg Trp Phe Leu
        755                 760                 765

Arg Ala Leu Leu Leu Glu Arg Met Val Pro Trp Ile Pro Ala Lys Arg
    770                 775                 780

Thr Phe Arg Ser Lys Ile Ala Tyr Gly Pro Ser Leu Pro Ile Ser Leu
785                 790                 795                 800

Arg Arg Thr Lys Thr Pro Ser Ser Thr Pro Thr Leu Arg Cys Leu Thr
                805                 810                 815

Gln Met Leu Trp Met Ser Gln Leu Val His Gln Arg Gln Val Arg Lys
            820                 825                 830

Ile Ser Leu Arg Pro Pro Ile Pro Cys Arg Glu Thr Ala Ile Phe Ile
        835                 840                 845

Cys Val Pro Ile Trp Leu Ile Ile Arg Ala Ile Ser Ser Thr Ser Pro
    850                 855                 860

Val Arg Gln Gln Val Ile Ser Lys Tyr Ser Arg Thr Pro Val Pro Ala
865                 870                 875                 880

Arg Gln Gln Glu Ile Ala Leu His Trp Gln Arg Ala Ala Val Met Leu
                885                 890                 895

His Leu Arg Trp Ala Met Pro Glu Ala Leu Leu Ile Ser Val Arg Met
            900                 905                 910

Asn Ile Pro Cys Trp Ile Met Ala Thr Ile Ala Gly Val Trp Gln Arg
        915                 920                 925

Ile Ala Arg Lys Leu Pro Leu Gln Pro Leu Met Cys Ile Trp Arg Pro
    930                 935                 940

His Asn Arg Trp Tyr Leu Met Gln Asn Trp Thr Pro Cys Val Ser Val
945                 950                 955                 960

Leu Val Ala Lys Ala Leu Val Thr Ile Arg Arg Cys Gly Val Arg Gln
                965                 970                 975

Leu Thr Pro Ala Thr Thr Pro Leu Met Arg Glu Leu Val Leu Ser Lys
            980                 985                 990

His Arg Ala Arg Ser Val Ser Ile  Ala Val Ser Pro Val  Lys Lys Ala
        995                 1000                1005

Val Gln  Phe Ala Ala Ser Leu  Val Thr Leu Ile Leu  Ile Leu Val
    1010                1015                1020

Leu Ile  Ala Ala Ala Lys Val  Ile Ser Ile Ala Ile  Pro Trp Gly
    1025                1030                1035
```

-continued

```
Leu Met  Pro Val Gly Ser Ile  Arg Thr Val Pro Met  Leu Met Gly
    1040                 1045                 1050

Trp Lys  Leu Thr Val Leu Pro  Thr Pro Ser Met Ala  Arg Val Met
    1055                 1060                 1065

Gly Gln  Gln Arg Leu Ala Ile  Thr Ile Val Thr Ala  Arg Val Leu
    1070                 1075                 1080

Met Leu  Arg Ala Gly Ser Val  Gly Leu Thr Asp Cys  Gly Val Leu
    1085                 1090                 1095

Asp Pro  Ile Trp Pro Leu Pro  Ala Leu Pro Gln Met  Val Arg Thr
    1100                 1105                 1110

Thr Arg  Tyr Gln Thr Ala Cys  Ala Arg Met Trp Glu  Ile Pro Gly
    1115                 1120                 1125

Tyr Tyr  Ala Leu Lys Arg Glu  Arg Arg Ala Ile Thr  Trp Thr Cys
    1130                 1135                 1140

Lys Thr  Val Arg Arg Trp Asn  Pro Gly Lys Arg Pro  Cys Val Arg
    1145                 1150                 1155

Asn Thr  Pro Ile Leu Thr Arg  Lys Leu Met Thr Met  Ala Asn Leu
    1160                 1165                 1170

Ile Met  Met Trp Leu Glu Pro  Val Ala Phe Ile Arg  Leu Val Gly
    1175                 1180                 1185

His Arg  Leu Pro Arg Arg Ala  Val Ile Cys Gln Ser  Ala Met Ala
    1190                 1195                 1200

Met Ala  Gln Gly Asn Arg Arg  Gly Ile Leu Arg Arg  Val Trp Ser
    1205                 1210                 1215

Gly Arg  Ser
    1220
```

<210> SEQ ID NO 7
<211> LENGTH: 3791
<212> TYPE: DNA
<213> ORGANISM: Artificial Sequence
<220> FEATURE:
<223> OTHER INFORMATION: Synthetic yejO mutated gene

<400> SEQUENCE: 7

```
atgcatcaat ctggttctgt ttctctttgt cgttccgcaa tatctgttct ggtggctaca     60
gcgttaagga aggtgcgaac aagtccctga tatgagatca tgtttgtcat ctggagccat    120
agaacagggt tcatcatgag tcatcaactt accttcgccg acagtgaatt cagcagtaag    180
cgccgtcaga ccagaaaaga gattttcttg tcccgcatgg agcagattct gccatggcaa    240
aacatggtgg aagtcatcga gccgttttac cccaaggctg gtaatggccg gcgaccttat    300
ccgctggaaa ccatgctacg cattcactgc atgcagcatt ggtacaacct gagcgatggc    360
gcgatggaag atgctctgta cgaaatcgcc tccatgcgtc tgtttgcccg gttatccctg    420
gatagcgcct tgccggaccg caccaccatc atgaatttcc gccacctgct ggagcagcat    480
caactggccc gccaattgtt caagaccatc aatcgctggc tggccgaagc aggcgtcatg    540
atgactcaag gcaccttggt cgatgccacc atcattgagg cacccagctc gaccaagaac    600
aaagagcagc aacgcgatcc ggagatgcat cagaccaaga aaggcaatca gtggcacttt    660
ggcatgaagg cccacattgg tgtcgatgcc aagagtggcc tgacccacag cctggtcacc    720
accgcggcca acgagcatga cctcaatcag ctgggtaatc tgctgcatgg agaggagcaa    780
tttgtctcag ccgatgccgg ctaccaaggg gcgccacagc gcgaggagct ggccgaggtg    840
gatgtggact ggctgatcgc cgagcgcccc ggcaaggtaa gaaccttgaa acagcatcca    900
```

-continued

```
cgcaagaaca aaacggccat caacatcgaa tacatgaaag ccagcatccg ggccagggtg    960
gagcacccat ttcgcatcat caagcgacag ttcggcttcg tgaaagccag atacaagggg   1020
ttgctgaaaa acgataacca actggcgatg ttattcacgc tggccaacct gtttcgggcg   1080
gaccaaatga tacgtcagtg ggagagatct cactaaaaac tggggataac gccttaaatg   1140
gcgaagaaac ggtctaaata ggctgattca aggcatttac gggagaaaaa atcggctcaa   1200
acatgaagaa atgaaatgac tgagtcagcc gagaagaatt tccccgctta ttcgcacctt   1260
ccttatattc acccatagca ttggcatcaa ctgttgagta tggtgagaca gttgatggtg   1320
ttgtcctgga aaaagatatc cagctggttt atgggaccgc caataatacg aaaatcaatc   1380
ctggcggaga acagcatata aaagaatttg gtgtaagtaa taatactgaa attaacggag   1440
ggtatcagta cattgaaatg aatggcgccg cagaatactc agtattaaat gacggttatc   1500
aaattgttca aatgggtggc gcggcaaacc agactacgct caataatggt gtgctacagg   1560
tttatggcgc agcgaatgat accacgatta aaggcgggcg cttaatcgtt gaaaaagatg   1620
ggggggccgt ctttgtcgct atcgaaaagg gaggactact ggaggttaaa gagggggat    1680
ttgcatttgc ggtagatcag aaagcaggcg gtgctattaa aacaaccacg cgggccatgg   1740
aggtattcgg aacaaaccgt ctcggtcagt tcgatatcaa gaatggtatt gctaataata   1800
tgttgttgga aaacggcgga agtttgcgag ttgaagaaaa tgacttcgct tataatacca   1860
ctgtagatag tggcggctta ctggaggtta tggatggcgg gactgtaact ggcgttgata   1920
aaaaagcagg cggaaaatta attgtctcaa cgaatgcgct ggaagtgagt ggtccaaaca   1980
gtaaaggcca atttagtata aaagatggtg tgtcaaaaaa ttatgaactg gatgatggtt   2040
ccgggctcat tgttatggag gacacgcagg ccattgatac tatccttgat aagcatgcca   2100
ctatgcaatc gctgggaaag gatactggta cgaaagtgca ggcaaatgcg gtatatgatc   2160
tcggtcgatc atatcagaat ggaagtatca cgtattcctc aaaagccatc tctgaaaata   2220
tggttatcaa caatggccgc gctaacgtct gggctggcac aatggttaac gtttcagtca   2280
gagggaatga tggcattctt gaggtcatga agccgcaaat aaattatgca cccgcaatgt   2340
tggtgggtaa ggtagtggtt tctgagggcg cttcttttag aacgcatggt gccgtggata   2400
ccagcaaagc ggacgtttcg ctcgaaaata gcgtatggac catcattgcc gatatcacta   2460
cgacgaacca aaacaccctc ctcaacttag ccaaccttgc gatgtctgac gcaaatgtga   2520
ttatgatgga tgagccagtg actcgttcat cagtgacggc aagtgcggaa aatttcatta   2580
cgttgaccac caataccctg tcgggaaacg gcaattttta tatgcgtacc gatatggcta   2640
atcatcagag cgatcagctc aacgtcaccg gtcaggcaac aggtgatttc aaaatattcg   2700
tgacggacac cggtgccagc ccggcagcag gagatagcct tacactggta acaacgggcg   2760
gcggtgatgc tgcatttacg ttgggcaatg ccggaggcgt tgttgatatc ggtacgtatg   2820
aatatacctt gctggataat ggcaaccata gctggagtct ggcagagaat cgcgcgcaaa   2880
ttaccccttc aaccactgat gtgctgaata tggcggccgc acaaccgctg gtatttgatg   2940
cagaactgga caccgtgcgt gagcgtcttg gtagcgtaaa aggcgttagt tacgatacgg   3000
cgatgtggag ttcggcaatt aacacccgca acaacgtgac cactgatgcg ggagctggtt   3060
ttgagcaaac attgacgggc ctgacgctcg gtatcgatag ccgtttctcc cgtgaagaaa   3120
gcagtacaat tcgcggcttg atctttggtt actctcattc tgatattggt tttgatcgcg   3180
gcggcaaagg taatatcgat agctataccc tgggggctta tgccggttgg gagcatcaga   3240
```

-continued

```
acggtgccta tgttgatggg gtggtgaaag ttgaccgttt tgccaacacc atccatggca   3300

agatgagtaa tggggcaaca gcgtttggcg attacaatag taacggcgcg ggtgctcatg   3360

ttgagagcgg gttccgttgg gttgacggat tgtggagtgt tagaccctat ctggccttta   3420

ccggctttac cacagatggt caggactaca cgttatcaaa cggcatgcgc gcggatgtgg   3480

gaaatacccg gatattacgc gctgaagcgg gaacggcggt aagctatcac atggacctgc   3540

aaaacggtac gacgctggaa ccctggctga aagcggccgt gcgtcaggaa tacgccgatt   3600

ctaaccaggt gaaagttaat gacgatggca aatttaataa tgatgtggct ggaaccagtg   3660

gcgtttatca ggctggtata aggtcatcgt ttaccccgac gttaagcggt catttgtcag   3720

tcagctatgg caatggcgca ggggtagaat cgccgtggaa tactcaggcg ggtgtggtct   3780

ggacgttctg a                                                         3791
```

<210> SEQ ID NO 8
<211> LENGTH: 1221
<212> TYPE: PRT
<213> ORGANISM: Artificial Sequence
<220> FEATURE:
<223> OTHER INFORMATION: Synthetic yejO mutated protein

<400> SEQUENCE: 8

```
Met His Gln Ser Gly Ser Val Ser Leu Cys Arg Ser Ala Ile Ser Val
1               5                   10                  15

Leu Val Ala Thr Ala Leu Arg Lys Val Arg Thr Ser Pro Tyr Glu Ile
            20                  25                  30

Met Phe Val Ile Trp Ser His Arg Thr Gly Phe Ile Met Ser His Gln
        35                  40                  45

Leu Thr Phe Ala Asp Ser Glu Phe Ser Ser Lys Arg Arg Gln Thr Arg
    50                  55                  60

Lys Glu Ile Phe Leu Ser Arg Met Glu Gln Ile Leu Pro Trp Gln Asn
65                  70                  75                  80

Met Val Glu Val Ile Glu Pro Phe Tyr Pro Lys Ala Gly Asn Gly Arg
                85                  90                  95

Arg Pro Tyr Pro Leu Glu Thr Met Leu Arg Ile His Cys Met Gln His
            100                 105                 110

Trp Tyr Asn Leu Ser Asp Gly Ala Met Glu Asp Ala Leu Tyr Glu Ile
        115                 120                 125

Ala Ser Met Arg Leu Phe Ala Arg Leu Ser Leu Asp Ser Ala Leu Pro
    130                 135                 140

Asp Arg Thr Thr Ile Met Asn Phe Arg His Leu Leu Glu Gln His Gln
145                 150                 155                 160

Leu Ala Arg Gln Leu Phe Lys Thr Ile Asn Arg Trp Leu Ala Glu Ala
                165                 170                 175

Gly Val Met Met Thr Gln Gly Thr Leu Val Asp Ala Thr Ile Ile Glu
            180                 185                 190

Ala Pro Ser Ser Thr Lys Asn Lys Glu Gln Gln Arg Asp Pro Glu Met
        195                 200                 205

His Gln Thr Lys Lys Gly Asn Gln Trp His Phe Gly Met Lys Ala His
    210                 215                 220

Ile Gly Val Asp Ala Lys Ser Gly Leu Thr His Ser Leu Val Thr Thr
225                 230                 235                 240

Ala Ala Asn Glu His Asp Leu Asn Gln Leu Gly Asn Leu Leu His Gly
                245                 250                 255

Glu Glu Gln Phe Val Ser Ala Asp Ala Gly Tyr Gln Gly Ala Pro Gln
```

-continued

```
            260                 265                 270

Arg Glu Glu Leu Ala Glu Val Asp Val Asp Trp Leu Ile Ala Glu Arg
        275                 280                 285

Pro Gly Lys Val Arg Thr Leu Lys Gln His Pro Arg Lys Asn Lys Thr
    290                 295                 300

Ala Ile Asn Ile Glu Tyr Met Lys Ala Ser Ile Arg Ala Arg Val Glu
305                 310                 315                 320

His Pro Phe Arg Ile Ile Lys Arg Gln Phe Gly Phe Val Lys Ala Arg
                325                 330                 335

Tyr Lys Gly Leu Leu Lys Asn Asp Asn Gln Leu Ala Met Leu Phe Thr
            340                 345                 350

Leu Ala Asn Leu Phe Arg Ala Asp Gln Met Ile Arg Gln Trp Glu Arg
        355                 360                 365

Ser His Lys Leu Gly Ile Thr Pro Met Ala Lys Lys Arg Ser Lys Ala
    370                 375                 380

Asp Ser Arg His Leu Arg Glu Lys Lys Ser Ala Gln Thr Arg Asn Glu
385                 390                 395                 400

Met Thr Glu Ser Ala Glu Lys Asn Phe Pro Ala Tyr Ser His Leu Pro
                405                 410                 415

Tyr Ile His Pro His Trp His Gln Leu Leu Ser Met Val Arg Gln Leu
            420                 425                 430

Met Val Leu Ser Trp Lys Lys Ile Ser Ser Trp Phe Met Gly Pro Pro
        435                 440                 445

Ile Ile Arg Lys Ser Ile Leu Ala Glu Asn Ser Ile Lys Asn Leu Val
    450                 455                 460

Val Ile Ile Leu Lys Leu Thr Glu Gly Ile Ser Thr Leu Lys Met Ala
465                 470                 475                 480

Pro Gln Asn Thr Gln Tyr Met Thr Val Ile Lys Leu Phe Lys Trp Val
                485                 490                 495

Ala Arg Gln Thr Arg Leu Arg Ser Ile Met Val Cys Tyr Arg Phe Met
            500                 505                 510

Ala Gln Arg Met Ile Pro Arg Leu Lys Ala Gly Ala Ser Leu Lys Lys
        515                 520                 525

Met Gly Gly Pro Ser Leu Ser Leu Ser Lys Arg Glu Asp Tyr Trp Arg
    530                 535                 540

Leu Lys Arg Gly Asp Leu His Leu Arg Ile Arg Lys Gln Ala Val Leu
545                 550                 555                 560

Leu Lys Gln Pro Arg Gly Pro Trp Arg Tyr Ser Glu Gln Thr Val Ser
                565                 570                 575

Val Ser Ser Ile Ser Arg Met Val Leu Leu Ile Ile Cys Cys Trp Lys
            580                 585                 590

Thr Ala Glu Val Cys Glu Leu Lys Lys Met Thr Ser Leu Ile Ile Pro
        595                 600                 605

Leu Ile Val Ala Ala Tyr Trp Arg Leu Trp Met Ala Gly Leu Leu Ala
    610                 615                 620

Leu Ile Lys Lys Gln Ala Glu Asn Leu Ser Gln Arg Met Arg Trp Lys
625                 630                 635                 640

Val Val Gln Thr Val Lys Ala Asn Leu Val Lys Met Val Cys Gln Lys
                645                 650                 655

Ile Met Asn Trp Met Met Val Pro Gly Ser Leu Leu Trp Arg Thr Arg
            660                 665                 670

Arg Pro Leu Ile Leu Ser Leu Ile Ser Met Pro Leu Cys Asn Arg Trp
        675                 680                 685
```

-continued

```
Glu Arg Ile Leu Val Arg Lys Cys Arg Gln Met Arg Tyr Met Ile Ser
    690                 695                 700

Val Asp His Ile Arg Met Glu Val Ser Arg Ile Pro Gln Lys Pro Ser
705                 710                 715                 720

Leu Lys Ile Trp Leu Ser Thr Met Ala Ala Leu Thr Ser Gly Leu Ala
                725                 730                 735

Gln Trp Leu Thr Phe Gln Ser Glu Gly Met Met Ala Phe Leu Arg Ser
            740                 745                 750

Ser Arg Lys Ile Met His Pro Gln Cys Trp Trp Val Arg Trp Phe Leu
        755                 760                 765

Arg Ala Leu Leu Leu Glu Arg Met Val Pro Trp Ile Pro Ala Lys Arg
    770                 775                 780

Thr Phe Arg Ser Lys Ile Ala Tyr Gly Pro Ser Leu Pro Ile Ser Leu
785                 790                 795                 800

Arg Arg Thr Lys Thr Pro Ser Ser Thr Pro Thr Leu Arg Cys Leu Thr
                805                 810                 815

Gln Met Leu Trp Met Ser Gln Leu Val His Gln Arg Gln Val Arg Lys
            820                 825                 830

Ile Ser Leu Arg Pro Pro Ile Pro Cys Arg Glu Thr Ala Ile Phe Ile
        835                 840                 845

Cys Val Pro Ile Trp Leu Ile Ile Arg Ala Ile Ser Ser Thr Ser Pro
    850                 855                 860

Val Arg Gln Gln Val Ile Ser Lys Tyr Ser Arg Thr Pro Val Pro Ala
865                 870                 875                 880

Arg Gln Gln Glu Ile Ala Leu His Trp Gln Arg Ala Ala Val Met Leu
                885                 890                 895

His Leu Arg Trp Ala Met Pro Glu Ala Leu Leu Ile Ser Val Arg Met
            900                 905                 910

Asn Ile Pro Cys Trp Ile Met Ala Thr Ile Ala Gly Val Trp Gln Arg
        915                 920                 925

Ile Ala Arg Lys Leu Pro Leu Gln Pro Leu Met Cys Ile Trp Arg Pro
    930                 935                 940

His Asn Arg Trp Tyr Leu Met Gln Asn Trp Thr Pro Cys Val Ser Val
945                 950                 955                 960

Leu Val Ala Lys Ala Leu Val Thr Ile Arg Arg Cys Gly Val Arg Gln
                965                 970                 975

Leu Thr Pro Ala Thr Thr Pro Leu Met Arg Glu Leu Val Leu Ser Lys
            980                 985                 990

His Arg Ala Arg Ser Val Ser Ile  Ala Val Ser Pro Val  Lys Lys Ala
        995                 1000                1005

Val Gln  Phe Ala Ala Ser Leu  Val Thr Leu Ile Leu  Ile Leu Val
    1010                1015                1020

Leu Ile  Ala Ala Ala Lys Val  Ile Ser Ile Ala Ile  Pro Trp Gly
    1025                1030                1035

Leu Met  Pro Val Gly Ser Ile  Arg Thr Val Pro Met  Leu Met Gly
    1040                1045                1050

Trp Lys  Leu Thr Val Leu Pro  Thr Pro Ser Met Ala  Arg Val Met
    1055                1060                1065

Gly Gln  Gln Arg Leu Ala Ile  Thr Ile Val Thr Ala  Arg Val Leu
    1070                1075                1080

Met Leu  Arg Ala Gly Ser Val  Gly Leu Thr Asp Cys  Gly Val Leu
    1085                1090                1095
```

-continued

```
Asp Pro  Ile Trp Pro Leu Pro  Ala Leu Pro Gln Met  Val Arg Thr
    1100                 1105                 1110

Thr Arg  Tyr Gln Thr Ala Cys  Ala Arg Met Trp Glu  Ile Pro Gly
    1115                 1120                 1125

Tyr Tyr  Ala Leu Lys Arg Glu  Arg Arg Ala Ile Thr  Trp Thr Cys
    1130                 1135                 1140

Lys Thr  Val Arg Arg Trp Asn  Pro Gly Lys Arg Pro  Cys Val Arg
    1145                 1150                 1155

Asn Thr  Pro Ile Leu Thr Arg  Lys Leu Met Thr Met  Ala Asn Leu
    1160                 1165                 1170

Ile Met  Met Trp Leu Glu Pro  Val Ala Phe Ile Arg  Leu Val Gly
    1175                 1180                 1185

His Arg  Leu Pro Arg Arg Ala  Val Ile Cys Gln Ser  Ala Met Ala
    1190                 1195                 1200

Met Ala  Gln Gly Asn Arg Arg  Gly Ile Leu Arg Arg  Val Trp Ser
    1205                 1210                 1215

Gly Arg  Ser
    1220
```